United States Patent [19]

Slusarchyk et al.

[11] Patent Number: 5,185,459

[45] Date of Patent: Feb. 9, 1993

[54] BIS PROTECTED (HYDROXYMETHYL)CYCLOBUTANOLS

[75] Inventors: William A. Slusarchyk, Skillman; Robert Zahler, Pennington, both of N.J.

[73] Assignee: E. R. Squibb & Sons Inc., Princeton, N.J.

[21] Appl. No.: 888,062

[22] Filed: May 26, 1992

Related U.S. Application Data

[60] Division of Ser. No. 656,391, Feb. 19, 1991, Pat. No. 5,130,462, which is a division of Ser. No. 322,375, Mar. 13, 1989, which is a continuation-in-part of Ser. No. 175,376, Mar. 30, 1988, abandoned.

[51] Int. Cl.$^5$ .................. C07F 7/08; C07C 43/13; C07C 69/34
[52] U.S. Cl. .................. 556/449; 556/436; 560/193; 560/106; 560/231; 568/660
[58] Field of Search .................. 568/660; 556/449, 436; 560/193, 106, 231

[56] References Cited

U.S. PATENT DOCUMENTS

| | | | |
|---|---|---|---|
| 3,379,770 | 4/1968 | Elam et al. | 568/660 |
| 4,177,348 | 12/1979 | Shealy et al. | 544/317 |
| 4,232,154 | 11/1980 | Shealy et al. | 544/250 |
| 4,617,304 | 10/1986 | Ashton et al. | 544/320 |
| 4,743,689 | 5/1988 | Shimada | 544/277 |
| 4,782,062 | 11/1988 | Tolman et al. | 514/262 |
| 4,801,710 | 1/1989 | Mac Coss et al. | 544/244 |
| 4,855,466 | 8/1989 | Zahler et al. | 544/244 |
| 4,918,075 | 4/1990 | Zahler et al. | 514/262 |
| 4,968,674 | 11/1990 | Taniyama et al. | 514/63 |
| 5,064,961 | 11/1991 | Bisacchi et al. | 544/276 |

FOREIGN PATENT DOCUMENTS

| | | |
|---|---|---|
| 182315 | 5/1986 | European Pat. Off. |
| 358154 | 3/1990 | European Pat. Off. |
| 366059 | 5/1990 | European Pat. Off. |
| 2208295 | 9/1987 | Japan |

OTHER PUBLICATIONS

Peterson et al., "The Chemistry of Photodimers of Maleic and Furmaic Acid Derivatives", *The Journal of Organic Chemistry*, vol. 33, pp. 1018–1021 (1968).
N. Shimada et al., Oxetanocin, A Novel Nucleoside from Bacteria, Nov. 1986, J. Antibiotics 39, p. 1623.
H. Nakamura et al., The X-Ray Structure Determination of Oxetanocin, Nov. 1986, J. Antibiotics, 39, p. 1626.
H. Hoshino et al., Inhibition of Infectivity of Human Immunodeficiency Virus by Oxetanocin, Jul. 1987, J. Antibiotics, 40, p. 1077.
S. Niitsuma et al., Studies on the Total Synthesis of Oxetanocin; Tetrahedron Letters, vol. 28, pp. 4713–4714, May 1987.
G. N. Austin et al., Chiral Oxetanes from Sugar Lactones, Tetrahedron Letters, vol. 28, pp. 4741–4744, May 1987.
N. Shimada et al.—Derivatives of Oxetanocin: Oxetanocins, H, X and G, and 2-Aminooxetanocin A, J. Antibiotics, vol. 40, p. 1789, Dec. 1987.
Walton, "3-Methylenecyclobutyl, Cyclopent-3-enyl . . . ", J.Chem.Soc. Perkin Trans II 1987 pp. 231–235.
Kirmse et al., "2-Oxabicyclo[2.1.1]hexan . . . ", Chemische Berichte, vol. 121, No. 5, 1988, pp. 1013–1016.
Hanack et al., "Solvolysan von delta$^2$-cyclobutylmethyltosylat", Chemische Berichte, vol. 100, No. 6, 1967, pp. 2107–2116.
DeClerq, "Pyrimidine Nucleoside Analogs As Antiviral Agents" Targets For The Design of Antiviral Agents, 1983, pp. 203–230.
Bamford et al., "Synthesis and Antiviral Acitivty . . . " J. Med. Chem., 1990, vol. 33, pp. 2494–2501.
Kono et al., "Substrate Specificity Of A Thymidine . . . " Chem. Pharm. Bull., vol. 32 (1984), pp. 1919–1921.
March, "Advanced Organic Chemistry", 1985, p. 129.
Niitsuma et al., "Studies On The Total Synthesis . . . " Tetrahedron Letters, vol. 28, pp. 3967–3970 (1987).
Marquez et al., "Carbocyclic Nucleosides", Medicinal Research Review, vol. 6, pp. 1–16 and 36–40.
Shealy et al., "Synthesis and Antiviral Activity . . . ", J. Med. Chem., vol. 27, pp. 1416–1421 (1984).

*Primary Examiner*—Howard T. Mars
*Assistant Examiner*—Margaret J. Page
*Attorney, Agent, or Firm*—Stephen B. Davis

[57] ABSTRACT

Cyclobutanols of the formula

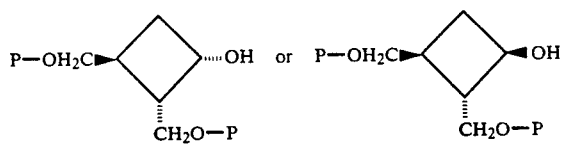

wherein P is a hydroxy protecting group are useful intermediates in the preparation of antiviral compounds.

2 Claims, No Drawings

BIS PROTECTED (HYDROXYMETHYL)CYCLOBUTANOLS

PRIOR APPLICATIONS

This application is a division of Ser. No. 656,391 filed Feb. 19, 1991 now U.S. Pat. No. 5,130,462 which is a division of Ser. No. 322,375 filed Mar. 13, 1989, which is a continuation-in-part of abandoned application Ser. No. 175,376 filed Mar. 30, 1988.

BRIEF DESCRIPTION OF THE INVENTION

Antiviral activity is exhibited by compounds having the formula

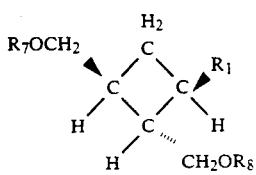

and its pharmaceutically acceptable salts. In formula I, and throughout the specification, the symbols are as defined below.

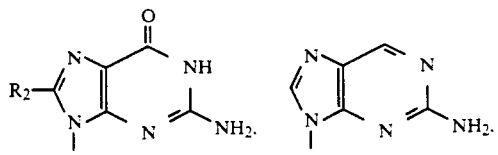

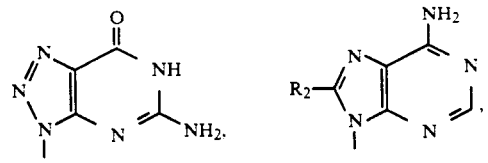

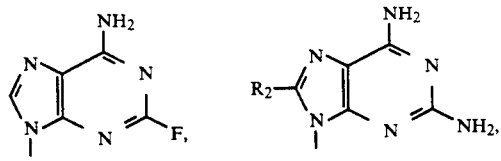

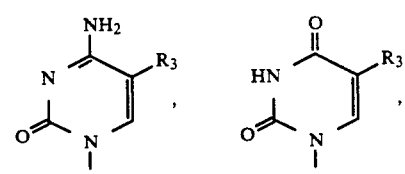

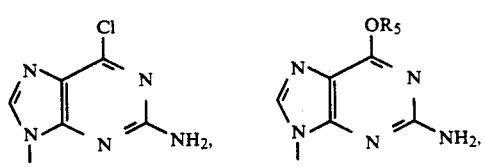

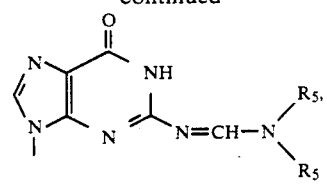

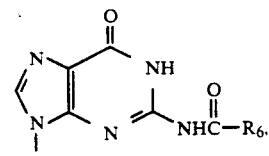

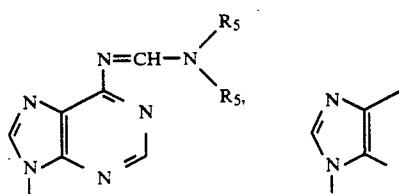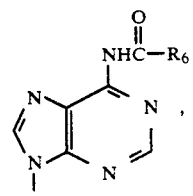

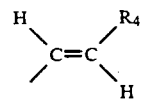

wherein $R_2$ is hydrogen, methyl, fluoro, chloro, bromo, iodo, hydroxy or amino; $R_3$ is fluoro, chloro, bromo, iodo, hydrogen, methyl, trifluoromethyl, ethyl, n-propyyl, 2-fluoroethyl, 2-chloroethyl, or $$\begin{matrix} H & R_4 \\ \diagdown & \diagup \\ C=C \\ \diagup & \diagdown \\ & H \end{matrix}$$

wherein $R_4$ is chloro, bromo, iodo, hydrogen methyl or trifluoromethyl; $R_5$ is alkyl; $R_6$ is hydrogen, alkyl, substituted alkyl, or aryl; and $R_7$ and $R_8$ are independently hydrogen,

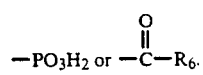

Preferred compounds of formula 1 are when $R_1$ is

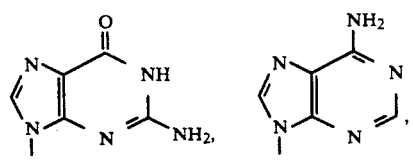

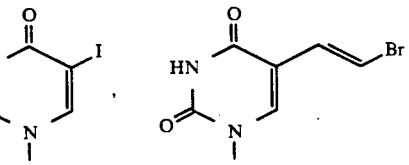

-continued

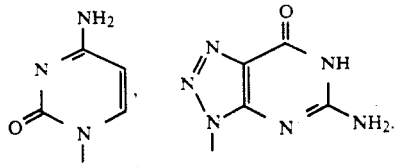

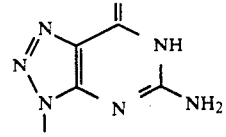

and

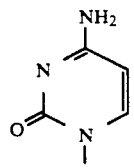

Most preferred compounds of formula 1 are when $R_1$ is

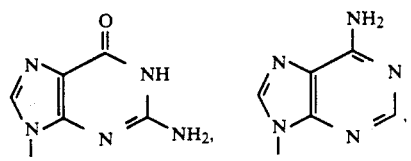

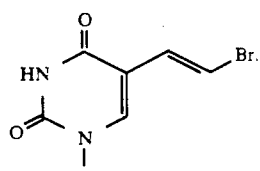

The term "alkyl" refers to both straight and branched chain groups. Those groups having 1 to 10 carbons are preferred. The term "substituted alkyl" refers to alkyl groups having one or more substituents. Preferred substituents are halogen, amino, azido, hydroxy, cyano, trialkylammonium (wherein each alkyl group has 1 to 6 carbons), alkoxy of 1 to 6 carbons, aryl and carboxy. The term "aryl" refers to phenyl and phenyl substituted with one, two or three substituents. Preferred substitutents are alkyl of 1 to 6 carbons, alkoxy of 1 to 6 carbons, halogen, trifluoromethyl, amino, alkylamino, dialkylamino, nitro, cyano, alkanoyloxy of 2 to 11 carbons, carboxy, carbamoyl and hydroxy.

DETAILED DESCRIPTION OF THE INVENTION

The compounds of formula 1, and the pharmaceutically acceptable salts thereof, are antiviral agents that can be used to treat viral infection in mammalian species such as domesticated animals (e.g., dogs, cats, horses and the like) and humans, and avian species (e.g., chickens and turkeys). The compounds of formula 1 wherein $R_1$ is

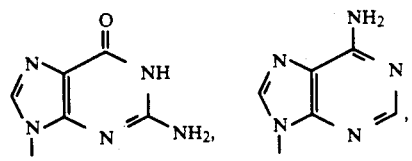

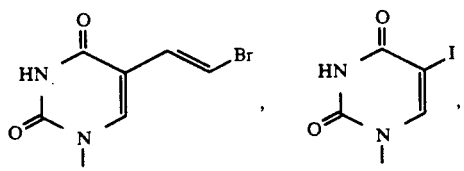

are effective against one or more of the following viruses: herpes simplex virus 1 and 2, varicellazoster viruses, cytomegalovirus, vaccinia virus, murine leukemia virus and human immunodeficiency virus (HIV). They are also believed to be active against a variety of other DNA and retroviruses. Exemplary DNA viruses in addition to those named above include other herpes viruses (e.g., Epstein-Barr virus, pseudorabies virus, and the like), other poxviruses (e.g. monkey pox and myoma), papovaviruses (e.g., the papilloma viruses), hepatitis B virus, and adenoviruses. Exemplary retroviruses in addition to those named above include those effecting man, such as human T-cell lymphotropic viruses (HTLV), and those effecting other animals, such as feline leukemia virus and equine infectious anemia virus. All of the other compounds of formula 1 with the exception of those wherein $R_1$ is

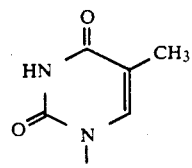

or

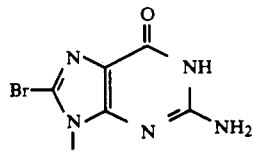

are believed to be active against one or more of the following viruses: herpes simplex virus 1 and 2, varicella-zoster virus, cytomegalovirus, and the retroviruses and other DNA viruses described above. The compounds of formula 1 wherein $R_1$ is

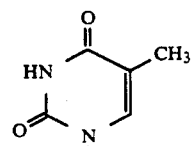

or

-continued

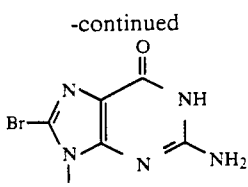

are believed to be active against the various DNA and retroviruses described above with the exception of herpes simplex virus 1 and 2, varicella-zoster virus and cytomegalovirus.

The compounds of this invention may be administered parenterally (for example, by intravenous, intraperitoneal or intramuscular injection), orally or topically depending on whether the preparation is used to treat internal or external viral infections.

For internal infections, the compounds may be administered orally or parenterally in an amount effective to treat the infection. The dosage will, of course, depend on the severity of the infection, but will likely be in the range of about 1.0 to 50 mg/kg of body weight. The desired dose may be administered several times daily at appropriate intervals.

For infections of the eye, or other external tissues, e.g. mouth and skin, the compositions may be applied to the infected part of the body of the patient topically as an ointment, cream, aerosol, gel, powder, lotion, suspension or solution (e.g. as in eye drops). The concentration of the compound in the vehicle will, of course, depend on the severity of the infection, but will likely be in the range of about 0.1 to 7% by weight.

A compound of formula 1 wherein $R_1$ is

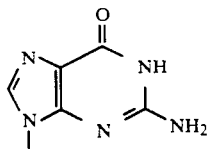

and $R_7$ and $R_8$ are hydrogen can be prepared from an intermediate of formula

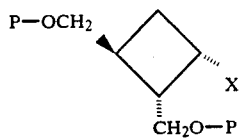
2 wherein P is a protecting group such as acyl, benzyl or silyl, and X is a leaving group such as chloro, bromo, iodo or an aryl or alkyl sulfonate well known in the art (e.g., p-toluenesulfonyloxy or methanesulfonyloxy). The term "acyl" refers to groups

wherein $R_9$ is a lower alkyl group of 1-6 branched or straight chain carbon atoms or a phenyl group. The term "silyl" refers to silyl protecting groups well known in the art [e.g., t-butyldimethylsilyl, t-butyldiphenylsilyl, (triphenylmethyl)dimethylsilyl, methyldiisopropylsilyl, or triisopropylsilyl].

Reaction of a compound of formula 2 with a protected form of guanine such as a compound of formula

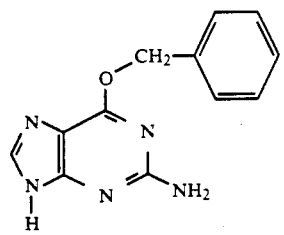
3 in the presence of a base such as potassium carbonate, sodium hydride, or potassium hydride in an aprotic polar solvent such as dimethylformamide, dimethyl sulfoxide, or sulfolane (tetramethylene sulfone) yields the corresponding compound of formula

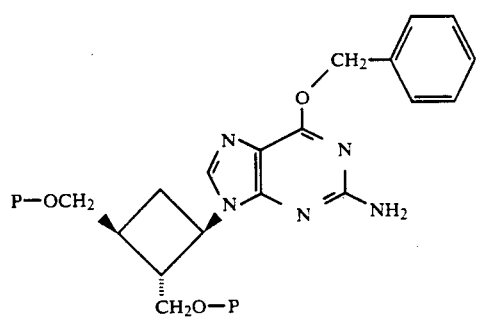
4

Optionally, the reaction can be run in the presence of a metal chelating catalyst such as 18-crown-6 (1,4,7,10,13,16-hexaoxacyclooctadecane) or 15-crown-5 (1,4,7,10,13-pentaoxacyclopentadecane). Removal of the protecting groups from a compound of formula 4 yields a compound of formula 1 wherein $R_1$ is

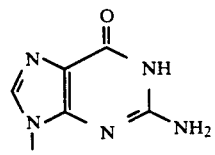

and $R_7$ and $R_8$ are hydrogen.

When the protecting group P in 4 is an acyl group, the protecting group P can be selectively removed using, for example, catalytic sodium methoxide in methanol or methanolic ammonia. Subsequent removal of the O-benzyl protecting group on the purine moiety can be accomplished by treatment with aqueous alcoholic mineral acid (e.g., aqueous methanolic hydrochloric acid), sodium in liquid ammonia, or by hydrogenolysis (e.g., palladium hydroxide on carbon in cyclohexene and ethanol). Alternatively, the purine O-benzyl protecting group can be removed initially, followed by removal of the acyl protecting groups.

When the group P in compound 4 is a silyl protecting group, removal of the P group can be accomplished using fluoride ion (e.g., tetrabutylammonium fluoride in tetrahydrofuran). The purine O-benzyl protecting group can then be removed with aqueous alcoholic mineral acid or by hydrogenolysis. When the protecting group P in 4 is benzyl, removal of all the benzyl protecting groups can be effected using either sodium in liquid ammonia or hydrogenolysis (e.g. palladium hydroxide on carbon in cyclohexene and ethanol). Alternatively, all of the benzyl protecting groups can be removed by treatment with boron trichloride in dichloromethane.

Reaction of a compound of formula 2 with compound

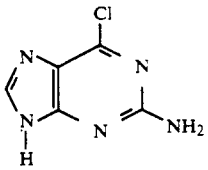

5 under conditions analogous to those used in the preparation of compound 4 provides a compound of formula

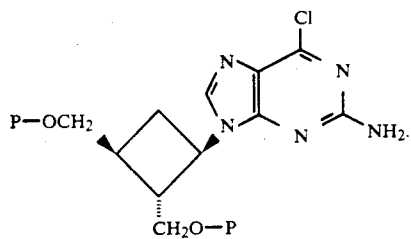

6

Selective removal of the protecting group P provides a compound of formula 1 wherein $R_1$ is

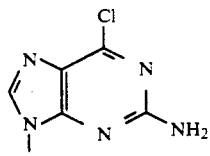

and $R_7$ and $R_8$ are hydrogen. For example, when the protecting group P in 6 is acyl, the P group can be selectively removed using, for example, catalytic sodium methoxide in methanol. When the protecting group P in 6 is silyl, the protecting group can be selectively removed by treatment with fluoride ion (e.g., tetrabutylammonium fluoride). When the protecting group P in 6 is benzyl, removal of the P group can be selectively performed by treatment with boron trichloride.

Acid hydrolysis (e.g., using hot aqueous hydrochloric acid) of the chloro group of a compound of formula 1 wherein $R_1$ is

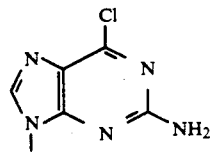

and $R_7$ and $R_8$ are hydrogen provides a compound of formula 1 wherein $R_1$ is

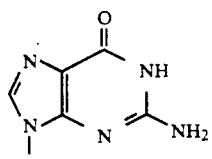

and $R_7$ and $R_8$ are hydrogen.

A compound of formula 2 can be prepared as follows: Reaction of diethyl fumarate and ketene diethyl acetal in hot t-butanol, yields a compound of formula 7 as a racemic mixture (see K.C. Brannock, et al., *J. Org. Chem.*, 29, 940 (1964)). Treatment of a compound of formula 7 with a reducing agent such as lithium aluminum hydride in a solvent such as diethyl ether or tetrahydrofuran yields diol 8. The hydroxyl groups can be protected with a protecting group "P" by methods known in the art, yielding a compound of formula 9. Deketalization of 9 using, for example, p-toluenesulfonic acid in acetone or aqueous sulfuric acid in acetonitrile, provides a compound of formula 10, which on treatment with a reducing agent (e.g. sodium borohydride or sodium cyanoborohydride in an alcohol such as methanol, ethanol, or isopropanol) affords a compound of formula 11 as the minor product, along with an isomeric compound of formula 12 as the major product, which can be separated by chromatography. Alternatively, a compound of formula 10 can be treated initially with lithium tri-sec-butylborohydride or lithium trisiamylborohydride in tetrahydrofuran, and then with aqueous hydrogen peroxide and sodium bicarbonate to give a compound of formula 11 as the major product and a compound of formula 12 (if present) as the minor product, which can be separated (if necessary) by chromatography. The compound of formula 11 can be converted to a compound of formula 2 by methods known in the art. For example, treatment of 11 with p-toluenesulfonyl chloride or methanesulfonyl chloride in pyridine yields a compound of formula 2 wherein X is p-toluenesulfonyloxy or methanesulfonyloxy, respectively. The compound of formula 2 wherein X is p-toluenesulfonyloxy or methanesulfonyloxy can also be prepared from the isomeric compound of formula 12 by treatment with p-toluenesulfonic acid or methanesulfonic acid, respectively, in the presence of triethylamine, triphenylphosphine, and diethyl or diisopropyl azodicarboxylate in a solvent such as toluene, ether or dioxane.

Alternatively, treatment of the compound of formula 12 with a methyltriphenoxyphosphonium halide or methyltriphenylphosphonium halide (i.e. chloride, bromide or iodide) in a solvent such as dimethylformamide provides a compound of formula 2 wherein X is chloro, bromo, or iodo. In yet another alternative, a compound of formula 2 wherein X is chloro, bromo, or iodo can be prepared from the compound of formula 12 using triphenylphosphine, diethyl (or diisopropyl) azodicarboxylate, and a source of halide such as methyl iodide, methyl bromide, or dichloromethane according to methodology known in the art. See, for example, H. Loibner, et al., *Helv. Chim. Acta.*, 59, 2100 (1976).

The above description is shown in the following schematic:

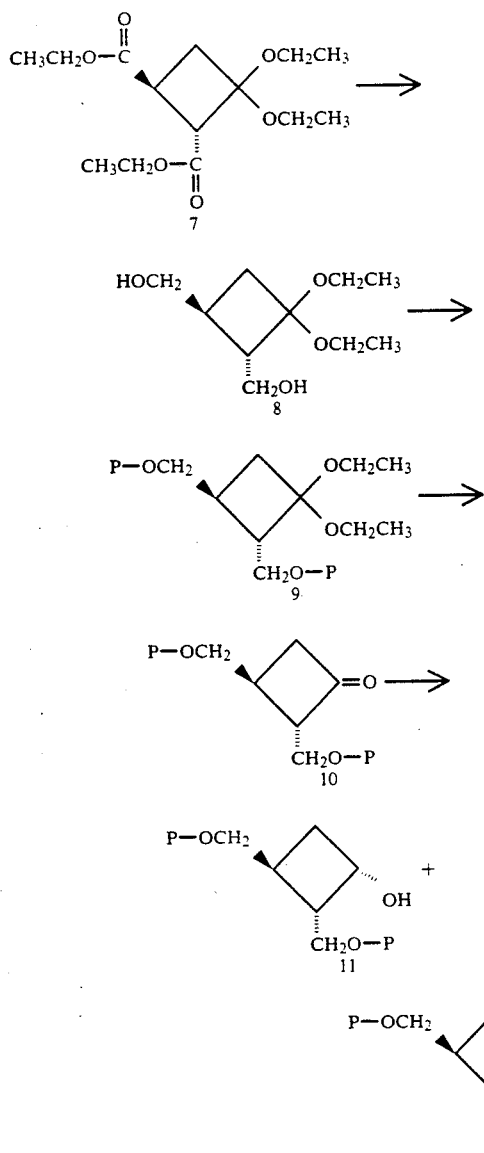

A compound of formula 1 wherein $R_1$ is

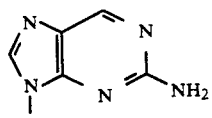

and $R_7$ and $R_8$ are hydrogen can be prepared from a compound of formula 6. For example, when the P group in 6 is an acyl or silyl protecting group, the chloro group can first be reduced by hydrogenation (e.g. ammonium formate and palladium on carbon in methanol or ethanol, palladium on carbon in cyclohexene and ethanol, or palladium on carbon, hydrogen and ethanol) and then the protecting groups P can be removed using either catalytic sodium methoxide in methanol or methanolic ammonia when P is acyl, and fluoride ion when P is silyl. Alternatively, the acyl or silyl protecting groups P can be removed first and then the chloro group can be reduced. When the protecting group P in 6 is benzyl, deprotection and reduction of the chloro group can be accomplished simultaneously by hydrogenolysis (e.g., palladium hydroxide on carbon in cyclohexene and ethanol; or ammonium formate or formic acid and palladium on carbon in methanol or ethanol).

Alternatively, this compound of formula 1 can be prepared by reacting an optionally protected compound of formula

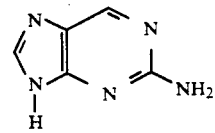

with a compound of formula 2 according to procedures analogous to those used in the preparation of a compound of formula 4, followed by removal of the protecting groups by methods known in the art. An optionally protected form of compound 13 can be protected at the amino (—NH$_2$) group by such exemplary groups as acyl, trityl, or substituted trityl. Exemplary substituted trityl groups are 4-monomethoxytrityl and 4,4'-dimethoxytrityl.

A compound of formula 1 wherein $R_1$ is

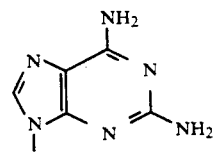

and $R_7$ and $R_8$ are hydrogen can be prepared from a compound of formula 6 by treatment with hot methanolic ammonia according to methods known in the art (e.g., J.C. Martin, et al., *J. Med. Chem.* 28, 358(1985)). When the protecting group P in 6 is acyl, for example, treatment with hot methanolic ammonia results in substitution of the chloro group by an amino group and simultaneous removal of the acyl protecting groups. When the protecting group P is a benzyl or silyl group, replacement of the chloro group by an amino group can be accomplished first, and then the protecting groups P can be removed (for example, by hydrogenolysis or treatment with boron trichloride in the case where P is benzyl, or by treatment with fluoride ion in the case where P is a silyl group).

Alternatively, this compound of formula 1 can be prepared by reacting an optionally protected compound of formula

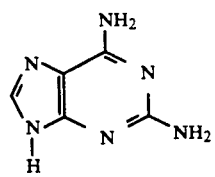

with a compound of formula 2 according to procedures analogous to those used in the preparation of a compound of formula 4, followed by removal of the protecting groups by methods known in the art. An optionally protected form of 14 can be protected at the amino (—NH₂) group by such exemplary groups as acyl, trityl or substituted trityl.

A compound of formula 1 wherein R₁ is

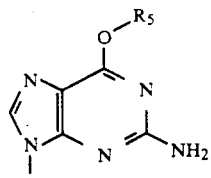

and R₇ and R₈ are hydrogen can be prepared from a compound of formula 6 or from a compound of formula 1- wherein R₁ is

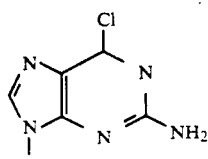

and R₇ and R₈ are hydrogen by methods known in the art. See, for example, J.F. Gerster, et al., *J. Amer. Chem. Soc.*, 87, 3752 (1965); K.K. Ogilvie, et al., *Can. J. Chem.*, 62, 2702 (1984); M.R. Harnden, et al., *J. Med. Chem.*, 30, 1636 (1987).

Alternatively, the compound of formula 1 can be prepared by reacting a compound of formula

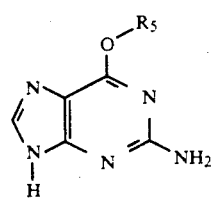

with a compound of formula 2 according to procedures analogous to those used in the preparation of a compound of formula 4, followed by removal of the protecting groups P by methods known in the art. The compound of formula 15 can be prepared from the compound of formula 5 by methods known in the art. See, for example, W.A. Bowles, et al., *J. Med. Chem.*, 6, 471 (1963); M. MacCoss, et al., *Tetrahedron Lett.*, 26, 1815 (1985).

Reaction of a compound of formula 2 with an optionally protected form of a compound of formula

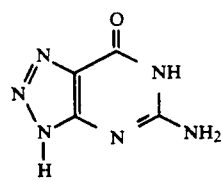

in the presence of a base such as potassium carbonate, sodium hydride, or potassium hydride in a polar aprotic solvent (e.g., dimethylformamide, dimethyl sulfoxide or sulfolane), in the optional presence of 18-crown-6 or 15-crown-5, gives, after removal of the protecting groups, the corresponding compound of formula 1 wherein R₁ is

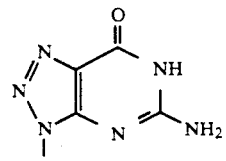

and R₇ and R₈ are hydrogen. The optionally protected forms of compound 16 can be protected at the amino (—NH₂) group by such exemplary groups as acyl, trityl, or substituted trityl Alternatively, reaction of a compound of formula 2 with a compound of formula

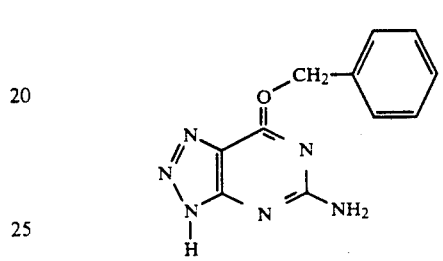

according to procedures analogous to those used in the preparation of a compound of formula 4, followed by removal of the protecting groups, provides the compound of formula 1 wherein R₁ is

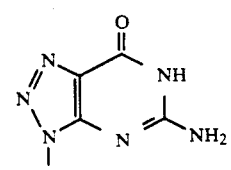

and R₇ and R₈ are hydrogen.

Alternatively, this compound of formula 1 can be prepared by reaction of 2 with a compound of the formula

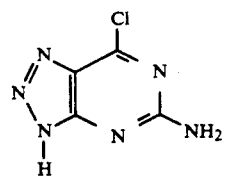

by procedures analogous to those used in the preparation of 4, followed by acid hydrolysis of the chloro group and simultaneous or subsequent removal of protecting groups P.

Reaction of the compound of formula 2 with a compound of formula

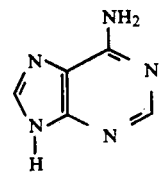

by methodology analogous to that used to prepare a compound of formula 4, and subsequent removal of the P protecting groups, yields the corresponding compound of formula 1 wherein $R_1$ is

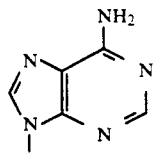

and $R_7$ and $R_8$ are hydrogen.

Alternatively, this compound of formula 1 can be prepared by reaction of a compound of formula

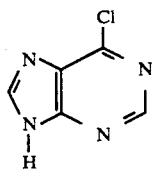

19 with a compound of formula 2 by methods analogous to those used in the preparation of a compound of formula 4. This affords the corresponding compound of formula

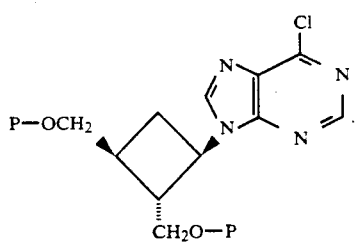

20

Treatment of a compound of formula 20 with hot ammonia in an alcohol (such as, methanol or ethanol) and simultaneous or subsequent deprotection of the P protecting groups yields the corresponding compound of formula 1 wherein $R_1$ is

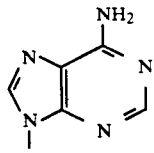

and $R_7$ and $R_8$ are hydrogen.

The compound of formula 1 wherein $R_1$ is

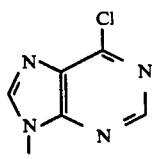

and $R_7$ and $R_8$ are hydrogen can be prepared from a compound of formula 20 by selective removal of the P protecting groups. For example, when the protecting group P in 20 is acyl, the P group can be selectively removed using, for example, catalytic sodium methoxide in methanol. When the protecting group P in 20 is silyl, the protecting group P can be selectively removed by treatment with fluoride ion (e.g., tetrabutylammonium fluoride). When the protecting group P in 20 is benzyl, removal of the P group can be selectively performed by treatment with boron trichloride.

Acid hydrolysis (e.g., using hot aqueous hydrochloric acid) or basic hydrolysis (e.g., aqueous methanolic sodium hydroxide) of the chloro group of a compound of formula 1 wherein $R_1$ is

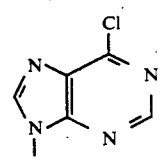

and $R_7$ and $R_8$ are hydrogen provides a compound of formula 1 wherein $R_1$ is

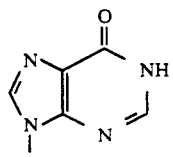

and $R_7$ and $R_8$ are hydrogen. Alternatively, this compound of formula 1 can be prepared by treatment of a compound of formula 1 wherein $R_1$ is

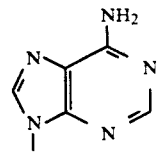

and $R_7$ and $R_8$ are hydrogen with adenosine deaminase according to methods known in the art (e.g., M.J. Robins, et al., *J. Med. Chem.*, 27, 1486 (1984); K.K. Ogilvie, et al., *Can. J. Chem.*, 62, 241 (1984)).

Compounds of formula 1 wherein $R_1$ is

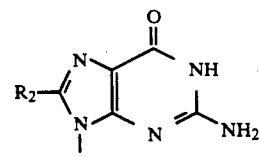

and $R_2$ is methyl, chloro, bromo, iodo, hydroxy, or amino, and $R_7$ and $R_8$ are hydrogen, can be prepared from the corresponding compound of formula 1 wherein $R_2$, $R_7$ and $R_8$ are hydrogen by methods known in the art.

The compound of formula 1 wherein $R_1$ is

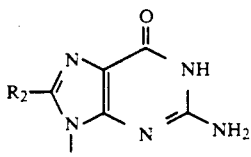

and $R_2$ is fluoro, and $R_7$ and $R_8$ are hydrogen, can be prepared from the corresponding compound of formula 1, wherein $R_2$ is bromo or iodo, and $R_7$ and $R_8$ are hydrogen. The amino ($-NH_2$) and/or hydroxyl groups can be optionally protected with acyl groups. Treatment with fluoride ion (e.g., sodium or potassium fluoride in a solvent such as dimethylformamide or diethylene glycol, or tetrabutylammonium fluoride in tetrahydrofuran) followed by removal (if necessary) of the optional acyl protecting groups using, for example, catalytic sodium methoxide in methanol or methanolic ammonia provides the compound of formula 1 wherein $R_1$ is

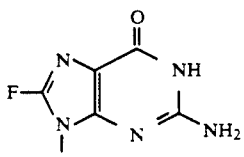

and $R_7$ and $R_8$ are hydrogen.

Compounds of formula 1 wherein $R_1$ is

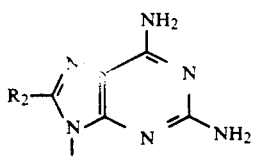

and $R_2$ is methyl, chloro, bromo, iodo, hydroxy, or amino, and $R_7$ and $R_8$ are hydrogen, can be prepared from the corresponding compound of formula 1 wherein $R_2$, $R_7$ and $R_8$ are hydrogen using procedures known in the art. The amino ($-NH_2$) and/or hydroxyl groups can be optionally protected by acyl groups.

The compound of formula 1 wherein $R_1$ is

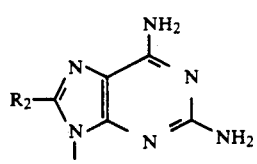

and $R_2$ is fluoro, and $R_7$ and $R_8$ are hydrogen, can be prepared from the corresponding compound of formula 1 wherein $R_2$ is bromo or iodo, and $R_7$ and $R_8$ are hydrogen. The amino ($-NH_2$) and/or hydroxyl groups can be optionally protected with acyl groups. Treatment with fluoride ion (e.g., sodium or potassium fluoride in a solvent such as dimethylformamide or diethylene glycol, or tetrabutylammonium fluoride in tetrahydrofuran) followed by removal (if necessary) of the optional acyl protecting groups, using, for example, catalytic sodium methoxide in methanol or methanolic ammonia, provides the compound of formula 1 wherein $R_1$ is

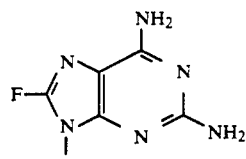

and $R_7$ and $R_8$ are hydrogen.

Compounds of formula 1 wherein $R_1$ is

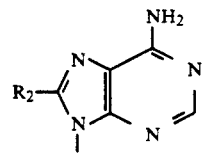

and $R_2$ is methyl, chloro, bromo, iodo, hydroxy, or amino and $R_7$ and $R_8$ are hydrogen, can be prepared from the corresponding compound of formula 1 wherein $R_2$, $R_7$ and $R_8$ are hydrogen following procedures known in the art. The amino ($-NH_2$) and/or hydroxyl groups can be optionally protected by acyl groups.

The compound of formula 1 wherein $R_1$ is

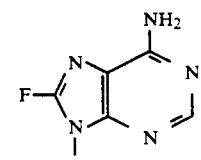

and $R_7$ and $R_8$ are hydrogen can be prepared from a compound of formula

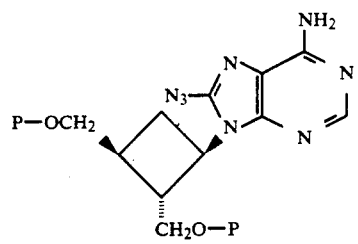

21

(wherein P is an acyl protecting group) by methodology known in the art. The compound of formula 21 can be prepared by known methods from the compound of the formula 1 wherein $R_1$ is

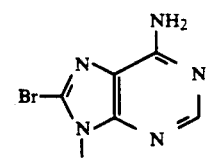

and $R_7$ and $R_8$ are hydrogen. The hydroxyl groups can be optionally protected by acyl groups.

For general methods of preparing 8-substituted purine nucleosides and nucleoside analogs see, for example: M.J. Robins, et al., *J. Med. Chem.*, 27, 1486 (1984);

R.E. Holmes, et al., *J. Amer. Chem. Soc.*, 86, 1242 (1964); R.A. Long, et al.. *J. Org. Chem.*, 32, 2751 (1967); R.E. Holmes, et al., *J. Amer. Chem. Soc.*, 87, 1772 (1965); M. Ikehara, et al., *Tetrahedron*, 26, 4251 (1970); H.J. Brentnall, et al., *Tetrahedron Lett.*, 2595 (1972); M. Ikehara, et al., *Chem. Pharm. Bull.*, 13, 1140 (1965); M. Ikehara, et al., *Chem. Commun.*, 1509 (1968).

The compound of formula 1 wherein $R_1$ is

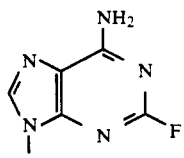

and $R_7$ and $R_8$ are hydrogen can be prepared from the compound of formula 1 wherein $R_1$ is

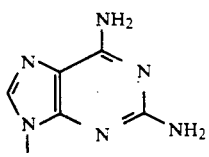

and $R_7$ and $R_8$ are hydrogen by following known procedures. See, for example, J.A. Montgomery et al.,in "Synthetic Procedures in Nucleic Acid Chemistry", Vol. 1, W. W. Zorbach and R.S. Tipson, Eds., Interscience Publishers (John Wiley and Sons), N.Y., p. 205, 1968.

The compound of formula

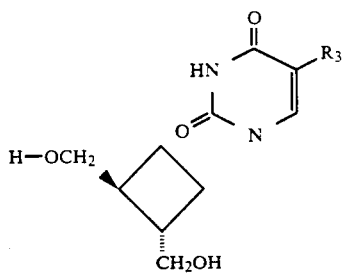

22 wherein $R_3$ is hydrogen, fluoro, methyl, ethyl, n-propyl, 2-chloroethyl, or 2-fluoroethyl can be prepared by reaction of the corresponding compound of formula

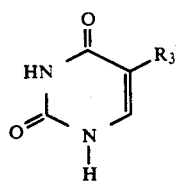

23 with a compound of formula 2 in the presence of a base such as potassium carbonate, sodium hydride, or potassium hydride, in an aprotic polar solvent (e.g., dimethylformamide, dimethylsulfoxide, or sulfolane), in the optional presence of 18-crown-6 or 15-crown-5, to yield an intermediate of formula

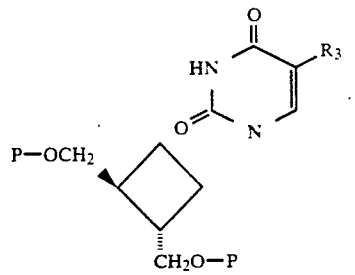

24

Removal of the protecting groups P provides the corresponding compound of formula 22. For example, when P is acyl, the protecting groups can be removed by treatment with sodium methoxide in methanol or methanolic ammonia, or when P is a silyl group, deprotection can be accomplished with fluoride ion. When P is a benzyl group, deprotection can be accomplished by hydrogenolysis (e.g., palladium hydroxide on carbon in cyclohexene and ethanol) or by treatment with boron trichloride.

The compound of formula 23 wherein $R_3$ is 2-chloroethyl or 2-fluoroethyl can be prepared by r methods known in the art [H. Griengl, et al., *J. Med. Chem.*, 30, 1199 (1987); *J. Med. Chem.*, 28, 1679 (1985)].

The compound of formula 22 wherein $R_3$ is fluoro can also be prepared from the corresponding compound 22 wherein $R_3$ is hydrogen and the hydroxy groups are optionally protected with a group such as acyl by fluorination with trifluoromethyl hypofluorite using methodology known in the art. For example, see M.J. Robins, et al., *J. Amer. Chem. Soc.*, 93, 5277 (1971) and *Chem. Communs.*, 18 (1972); T.S. Lin, et al., *J. Med. Chem.*, 26, 1691 (1983).

The compounds of formula 22 wherein $R_3$ is 2-chloroethyl and 2-fluoroethyl can also be prepared from a compound of formula

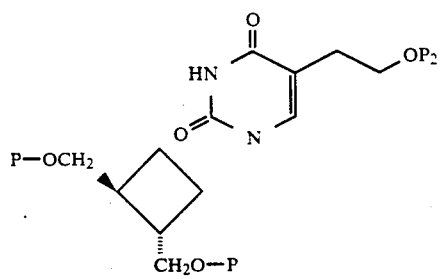

25 wherein $P_2$ and P are different protecting groups wherein $P_2$ can be selectively removed in the presence of P. For example, when $P_2$ is a silyl, trityl or substituted trityl group, P can be a benzyl or acyl group. Similarly, when $P_2$ is an acyl or benzyl group, P can be a silyl protecting group. Selective removal of the protecting group $P_2$ yields a compound of formula 24 wherein $R_3$ is 2-hydroxyethyl. Treatment of this compound with triphenylphosphine-carbon tetrachloride and subsequent removal of protecting groups P affords the compound of formula 22 wherein $R_3$ is 2-chloroethyl. Similar treatment using triphenylphosphineN-bromosuccinimide or triphenylphosphine N-bromosuccinimide-tetrabutylammonium iodide in place of triphenylphosphine-carbon tetrachloride (e.g., see H. Griengl, et al., *J. Med. Chem.*, 28, 1679 (1985)) affords compounds of formula 24 wherein $R_3$ is 2-bromoethyl or 2-iodoethyl, respectively. Subsequent treatment with fluoride ion, followed by removal of protecting groups P, provides the compound of formula 22 wherein R$_3$ is 2-fluoroethyl. When P is a silyl group, deprotection will occur upon treatment with fluoride ion. Alternatively, treatment of a compound of formula 24, wherein R$_3$ is 2-hydroxyethyl, with diethylaminosulfur trifluoride provides, upon removal of the protecting groups P, a compound of formula 22 wherein R$_3$ is 2-fluoroethyl.

The compound of formula 25 can be prepared by reaction of a compound of formula

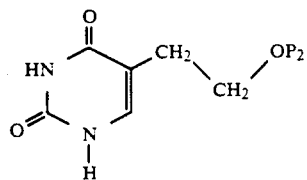
26 with a compound of formula 2 by methods analogous to those used for the preparation of 24 wherein, for example, R$_3$ is hydrogen, methyl or ethyl. The compound of formula 26 can be prepared from the corresponding free alcohol by methods known in the art.

The compound of formula

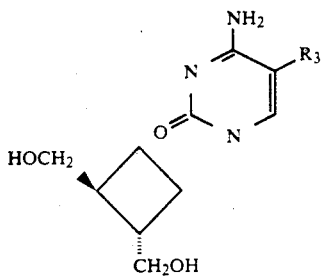
27 wherein R$_3$ is hydrogen, fluoro, methyl, ethyl, n-propyl, 2-chloroethyl, or 2-fluoroethyl can be prepared from the corresponding compound of formula 24 (wherein P, for example, is an acyl protecting group) by methods known in the art. See, for example, I. Wempner, et al.,in "Synthetic Procedures in Nucleic Acid Chemistry", Vol. 1, W.W. Zorbach and R.S. Tipson, Eds., Interscience Publishers, N.Y., p. 299, 1968; T.S. Lin, et al., *J. Med. Chem.*, 26, 1691 (1983); P. Herdewijn,et al., *J. Med. Chem.*, 28, 550 (1985). Deprotection using methanolic ammonia or sodium methoxide in methanol yields the corresponding compound of formula 27.

Alternatively, the compound of formula 27, wherein R$_3$ is fluoro, hydrogen, methyl, ethyl, n-propyl, 2-chloroethyl, or 2-fluoroethyl, can be prepared by reaction of the corresponding compound of formula

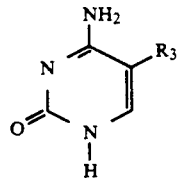
28 with a compound of formula 2 in the presence of a base such as potassium carbonate, sodium hydride, or potassium hydride in an aprotic solvent (e.g. dimethylformamide, dimethyl sulfoxide, or sulfolane), in the optional presence of 18-crown-6 or 15-crown-5, and subsequent removal of the protecting groups. Optionally, the amino ($-$NH$_2$) group in 28 can be protected, e.g., with an acyl group. Removal of this protecting group can be accomplished using sodium methoxide in methanol or methanolic ammonia.

Alternatively, the compound of formula 27 wherein R$_3$ is fluoro can be prepared from the corresponding compound wherein R$_3$ is hydrogen by fluorination with trifluoromethyl hypofluorite using methodology known in the art. Fluorination can also be performed on the compounds of formula 27 wherein R$_3$ is hydrogen and the hydroxyl and/or amino groups are protected, for example, by an acyl. After fluorination, deprotection using methanolic ammonia or aqueous hydroxide affords the compound of formula 27 wherein R$_3$ is fluoro. See, for example, M.J. Robins, et al., *J. Amer. Chem. Soc.*, 93, 5277 (1971) and *Chem. Commun.*, 18 (1972); T.S. Lin, et al., *J. Med. Chem.*, 26, 1691 (1983).

The compounds of formula 22 and 27 wherein R$_3$ is chloro, bromo, or iodo can be prepared from the corresponding compounds of formula 22 and 27 wherein R$_3$ is hydrogen by methods known in the art. See, for example, "Basic Principals in Nucleic Acid Chemistry", Vol. 1, P.O.P. Ts'O, Ed., Academic Press, N.Y., p. 146, 1974; P.K. Chang in "Nucleic Acid Chemistry" Part 3, L.B. Townsend and R.S. Tipson, Eds., John Wiley and Sons, N.Y., p.46, 1986.

The compounds of formula 22 and 27 wherein R$_3$ is trifluoromethyl can be prepared from the corresponding compounds of formula 22 and 27 wherein R$_3$ is iodo and the hydroxy and amino ($-$NH$_2$) groups are protected, for example, by an acyl, by treatment with trifluoromethyl iodide and copper according to procedures known in the art. Subsequent deprotection using methanolic ammonia or sodium methoxide in methanol yields the corresponding compound of formulas 22 and 27 wherein R$_3$ is trifluoromethyl. See, for example, Y. Kobayashi, et al., *J. Chem. Soc. Perkin* 1, 2755 (1980); S. Lin, et al., *J. Med. Chem.*, 26, 1691 (1983).

The compounds of formula 22 and 27 wherein R$_3$ is

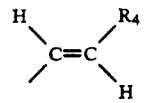

and R$_4$ is chloro, bromo, iodo, hydrogen, methyl or trifluoromethyl can be prepared from the corresponding compounds of formula 22 and 27 wherein R$_3$ is iodo or $-$HgCl via organopalladium intermediates. The compounds of formula 22 and 27 wherein R$_3$ is $-$HgCl can be prepared from the corresponding compounds of formula 22 and 27 wherein R$_3$ is hydrogen by methods known in the art. See, for example, references in E. DeClercq, et al., *Pharmac. Ther.*, 26, 1 (1984); M.E. Perlman, et al., *J. Med. Chem.*, 28, 741 (1985); P. Herdewijn, et al., *J. Med. Chem.*, 28, 550 (1985); D.E. Bergstrom, et al., *J. Med. Chem.*, 27, 279 (1984).

Compounds of formula 1 wherein R$_1$ is

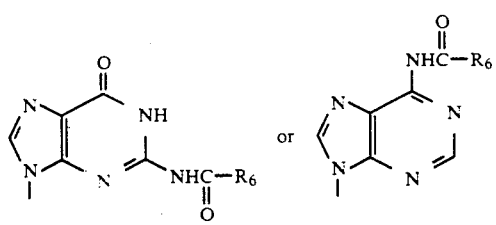

can be prepared from the corresponding compounds of formula 1 wherein R₁ is

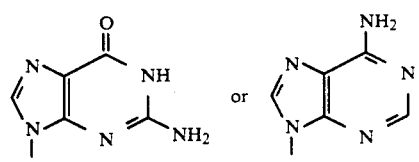

by methods known in the art.

Compounds of formula 1 wherein one or both R₇ and R₈ are

can be prepared by methods known in the art from the corresponding compounds of formula 1 wherein R₇ and R₈ are hydrogen.

For examples of acylation procedures see: "Synthetic Procedures in Nucleic Acid Chemistry", Vol. 1, W. W. Zorbach and R. S. Tipson, Eds., John Wiley and Sons, 1968; "Nucleic Acid Chemistry," Part 1, L.B. Townsend and R. S. Tipson, Eds., John Wiley and Sons, 1978; Y. Ishido, et al., *Nucleosides and Nucleotides*, 5, 159 (1986); J.C. Martin, et al., *J. Pharm. Sci.*, 76, 180 (1987); A. Matsuda, et al., *Synthesis*, 385 (1986).

Compounds of formula 1 wherein R₁ is

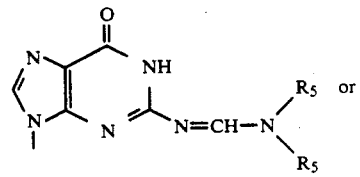

can be prepared from the corresponding compound of formula 1 wherein R₁ is

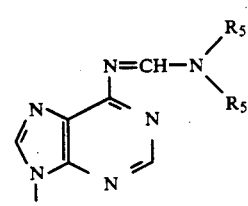

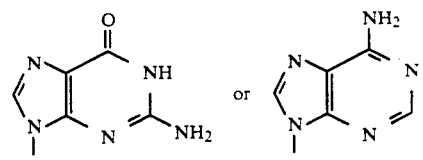

by procedures known in the art. See, for example, A. Holy and J. Zemlicka, *Collect. Czech. Chem. Commun.*, 32, 3159 (1967); K.K. Ogilvie, et al., *Nucleosides and Nucletides*, 4, 507 (1985); M.H. Caruthers, et al., *J. Amer. Chem. Soc.*, 108, 2040 (1986).

Compounds of the formula 1 wherein R₇ and/or R₈ are —PO₃H₂ can be prepared from the corresponding compounds of formula 1 wherein R₇ and R₈ are hydrogen by procedures known in the art. See, for example, H. Schaller, et al., *J. Amer. Chem. Soc.*, 85, 3821 (1963); J. Beres, et al., *J. Med. Chem.*, 29, 494 (1986); R. Noyori, et al., *Tet. Lett.*, 28, 2259 (1987); W. Pfeiderer, et al., *Helv. Chim. Acta.*, 70, 1286 (1987); "Nucleic Acid Chemistry". Part 2, L.B. Townsend and R.S. Tipson, Eds., John Wiley and Sons, 1978.

The stereochemistry shown for the compounds of this invention and intermediates leading to compounds of this invention is relative, not absolute. It is drawn to show that in the compounds of this invention, the base represented by R₁ is trans to the vicinal —CH₂OH substituent, and the —CH₂OH substituents are trans to each other The compounds of formula 1 wherein R₁ is

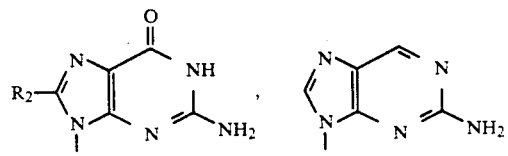

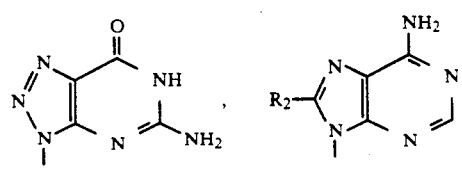

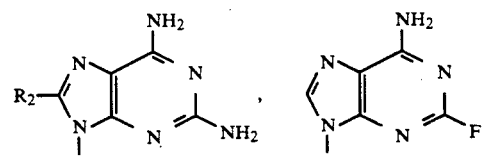

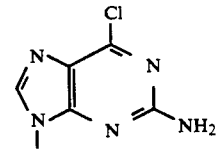

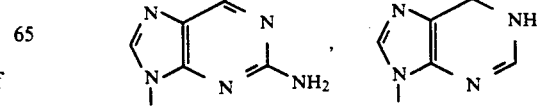

23
-continued

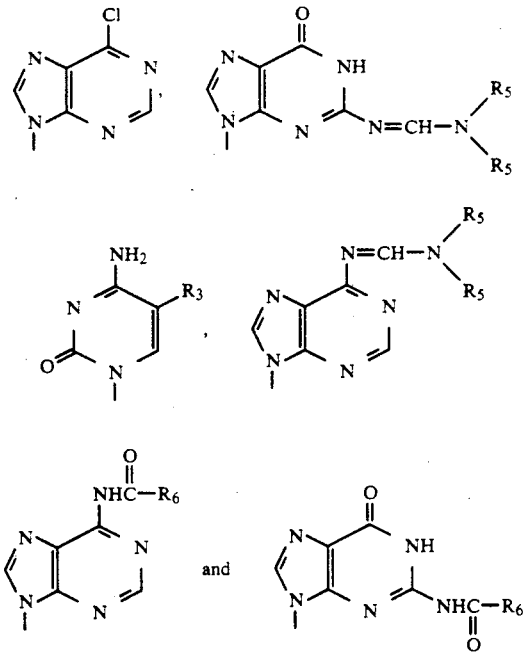

can form acid addition salts with inorganic or organic acids, Illustrative are the hydrohalide (e.g., hydrochloride and hydrobromide), alkylsulfonate, sulfate, phosphate and carboxylate salts.

The compounds of formula I wherein $R_1$ is

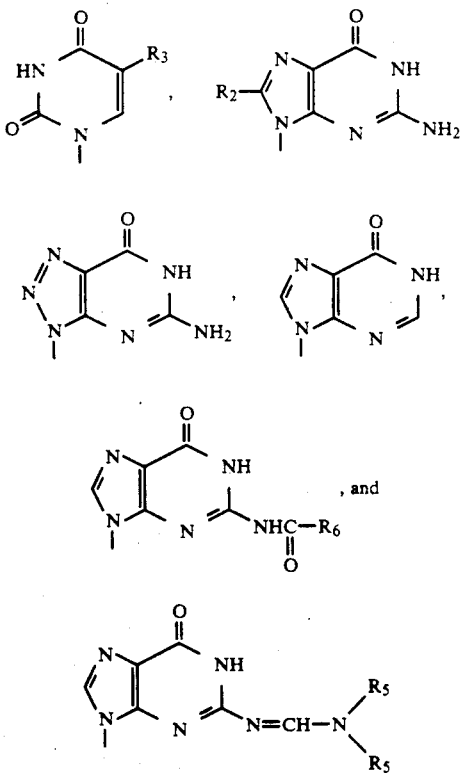

can form basic salts with inorganic and organic bases. Illustrative are alkali metal salts (e.g., sodium and potassium), alkaline earth metal salts (e.g. calcium and magnesium), ammonium and substituted ammonium salts.

The compounds of formula 1 wherein $R_7$ and/or $R_8$ are —$PO_3H_2$ can form basic salts with inorganic and organic bases. Illustrative are the alkali metal salts (e.g., sodium and potassium), alkaline earth metal salts (e.g., calcium and magnesium), ammonium and substituted ammonium salts.

The following examples are specific embodiments of this invention.

EXAMPLE 1

(1α, 2β, 3α)-9-[2,3-Bis(hydroxymethyl) cyclobutyl]guanine

A). Ketene Diethyl Acetal

This was prepared using the method described in "Organic Syntheses", Coll. Vol. III, E.C. Horning, Ed., John Wiley and Sons, N.Y. p 506 (1955). To a solution of potassium tert-butoxide (28.5 g, 0.254 mol) in dry tert-butanol (150 ml., dried over 3Å molecular sieves) at 50° was added bromoacetaldehyde diethyl acetal (38.5 ml, 0.254 mol). A column filled with glass helices (20×1.4 cm) with a total reflux partial take-off still head was placed on top of the reaction flask. The temperature of the oil bath was slowly raised to 100° C. After the reaction had refluxed for 35 minutes, the tert-butanol was distilled off over ca. 16 hours at a rate of 4.5 drops/min with a reflux ratio at the still head of 22:4.5. The oil bath was cooled to 20° and the helices-filled column was replaced by a short path distillation apparatus. Distillation at 20–50° and ca. 4 mm gave 26.96 g of a mixture containing 23.31 g of ketene diethyl acetal and 3.66 g of tert-butanol as determined by, $^1$H-NMR integration.

B). (trans)-3,3-Diethoxy-1,2-cyclobutanedicarboxylic acid, diethyl ester

This was prepared by modification of the method of K.C. Brannock, et al., J. Org. Chem., 29, 840 (1964). To a solution of 25.27g of the above mixture containing 21.63 g (0.186 mol) of ketene diethyl acetal in dry tert-butanol (60 ml) was added diethyl fumarate (28.28 ml, 0.173 mol). This was heated at 82° for 7 days. The reaction was concentrated in vacuo, and the residue was divided into portions of 3 g (A) and 39 g (B). Portion A was chromatographed on Merck silica gel-60 (1.5×30 cm) in 19:1 hexane:ethyl acetate. Fractions containing product were combined and concentrated to give 567 mg. Portion B was chromatographed twice on Merck silica gel-60 (35×5 cm) in the same solvent. Fractions containing product were combined and concentrated to give 10.43 g. The total yield of desired product was 10.99 g.

C). (trans)-3,3-Diethoxy-1,2-cyclobutanedimethanol.

To a suspension of lithium aluminum hydride (2.38 g, 0.0627 mol) in dry THF (50 ml) was added slowly (trans)-3,3-diethoxy-1,2-cyclobutanedicarboxylic acid, diethyl ester (11.29 g, 0.0392 mol) in THF (25 ml) so that a gentle reflux was maintained. The reaction was heated at 55° for 4 hours and then diluted with ether (100 ml) and poured into saturated aqueous ammonium chloride (100 ml). The pH was lowered to 4 with 3M sulfuric acid. The suspension was extracted with ether (4×100 ml) and then chloroform (3×100 ml). The ether extracts were combined, dried over sodium sulfate, filtered and concentrated to give 5.613 g of desired product. The chloroform extracts were combined, dried over sodium sulfate, filtered and concentrated to give 112 mg of additional desired product.

D). (trans)-3,3-Diethoxy-1,2-cyclobutanedimethanol, dibenzoate ester.

To a solution of (trans)-3,3-diethoxy-1, 2-cyclobutanedimethanol (5.7 g, 0.028 mol) in dry pyridine (40 ml) under nitrogenm at 0° was added, over 5 minutes, benzoyl chloride (9.73 ml. 0.0838 mol). This was warmed to room temperature and a recipitate formed. After 2 hours, water (20 ml) was added, and the reaction was stirred overnight. The solvents were removed in vacuo. The residue was dissolved in ethyl acetate (400 ml) and washed with water (2×150 ml), 1N hydrochloric acid (2×150 ml), and saturated sodium bicarbonate (3×150 ml). The organic layer was dried over sodium sulfate, filtered and concentrated to give 10.97 g of desired product.

E) (trans)-2,3-Bis[(benzoyloxy)methyl]cyclobutanone

To a solution of (trans)-3,3-diethoxy-1,2-cyclobutanedimethanol, dibenzoate eser (10.87 g, 0.0263 mol) in acetone (200 ml) was added p-toluenesulfonic acid (250 mg, 0.00132 mol). The reaction was refluxed for 3 hours. The solution was concentrated in vacuo. The residue was dissolved in ethyl acetate (200 ml) and washed with saturated sodium bicarbonate (2×200 ml). The aqueous layer was back extracted with ethyl acetate (50 ml). The organic layers were combined, dried over sodium sulfate, filtered and concentrated in vacuo to give 8.7 g of impure product. This residue was purified by column chromatography on Merck silica gel-60 (5×27 cm) eluting with hexane:ethyl acetate (5:1). Fractions containing the product were combined and concentrated to give 6.71 g of desired product.

Alternative preparation of (trans)-2,3-bis[(benzoyloxy)methyl]cyclobutanone

To a solution of (trans)-3,3-diethoxy-1,2cyclobutanedimethanol, dibenzoate ester (50 g, 0.12 mol) in 1.5 L of acetonitrile was added 570 ml of 0.5M sulfuric acid in water. The reaction was stirred under argon for 16 hours at 25° C., then was diluted with 5L of ethyl acetate. The mixture was washed with 2×1L of water, 2×1L of saturated sodium bicarbonate, 2×1L of water and finally 1L of brine. The organic phase was dried over sodium sulfate and concentrated to an oil. Trituration with hexane gave 34 g of crude product. Trituration of this crude solid with 300 ml of diethyl ether gave 10 g of desired product, mp 76–78° C. Chilling the filtrate at −30° C. for 4 hours gave 12 g of a second crop, mp 76–78° C., of equal purity.

F). (1α, 2β, 3α)-3-Hydroxy-1,2-cyclobutanedimethanol, 1,2-dibenzoate ester and (1α, 2β, 3α)-3-hydroxy-1,2-cyclobutanedimethanol, 1,2-dibenzoate ester.

To a solution of (trans)-2,3-bis[(benzoyloxy) methyl]cyclobutanone (2.46 g, 7.28 mmol) in dry methanol (40 ml) was added sodium cyanoborohydride (1.01 g, 16 mmol). Bromocresol green (3 mg) was added as a pH indicator. When the indicator turned blue, 1N HCl in methanol was added until the color turned yellow. After 5 hours, the color no longer changed, and the starting material was consumed. The solvent was removed in vacuo, and the residue was dissolved in ethyl acetate (100 ml) and washed with saturated sodium chloride (50 ml). The aqueous layer was back extracted with ethyl acetate (50 ml). The organic layers were combined, dried over sodium sulfate, filtered and concentrated in vacuo. The residue was purified by column chromatography on Merck silica gel-60 (5×55 cm).

Elution with hexane: ethyl acetate (7:3) gave 521 mg of (1α, 2β, 3α)-3-hydroxy-1,2-cyclobutanedimethanol,1,2-dibenzoate ester.

Elution with hexane: ethyl acetate (6:3) gave 1.78 g of (1α, 2β, 3α)-3-hydroxy-1,2-cyclobutanedimethanol,1,2-dibenzoate ester.

Alternative preparation of (1α, 2β, 3α)-3-hydroxy-1,2-cyclobutanedimethanol-,1,2-dibenzoate ester and (1α, 2β, 3α)-3-hydroxy-1,2-cyclobutanedimethanol-1,2-dibenzoate ester.

To a stirred solution of (trans)-2,3-bis[(benzoyloxy)-methyl]cyclobutanone (12.0 g, 0.0355 mol) in dry tetrahydrofuran at −78° under nitrogen was added 35.5 ml (0.0355 mol) of 1M lithium tri-sec-butylborohydride in tetrahydrofuran over 3 minutes. The reaction was warmed to room temperature, and then saturated aqueous sodium bicarbonate (34 ml) was added followed by dropwise addition of 30% hydrogen peroxide (13.0 ml, 0.127 mol) while keeping the reaction temperature at 30° using an ice water bath. The reaction was warmed to room temperature, stirred for 30 minutes, and diluted with ethyl acetate (400 ml) and water (120 ml). The layers were separated, and the organic layer was extracted with water (100 ml). An emulsion formed, and solid sodium chloride was added to separate the layers. The two water layers were combined and extracted with ethyl acetate. All ethyl acetate layers were combined, dried over sodium sulfate, filtered and concentrated in vacuo to a residue (12.5 g). A portion of this residue (7 g) was purified by preparative high pressure liquid chromatography on two Waters Prep Pak 500 silica gel cartridges eluting with 30% ethyl acetate in hexane at 250 ml/min. (1α, 2β, 3α)-3-hydroxy-1,2cyclobutanedimethanol, 1,2-dibenzoate ester eluted at 14–22 minutes, and (1α, 2β, 3α)-3-hydroxy-1,2-cyclobutanedimethanol, 1,2-dibenzoate ester eluted at 23–34 minutes. Similar chromatography of the remainder of the above 12.5 g residue (in two runs, one using 25% ethyl acetate in hexane and the other using 35% ethyl acetate in hexane) provided a total of 8.80 g of (1α, 2β, 3α)-3-hydroxy-1,2-cyclobutanedimethanol, 1,2-dibenzoate ester and 2.6 g of (1α, 2β, 3α)-3-hydroxy-1,2-cyclobutanedimethanol, dibenzoate ester.

Alternative preparation of (1α, 2β, 3α)-3-hydroxy-1,2-cyclobutanedimethanol1,2-dibenzoate ester.

To a solution of (trans)-2,3-bis-[(benzoyloxy)methyl]-cyclobutanone (13.15 g, 0.0389 mol) in tetrahydrofuran (180 ml) at −78° under nitrogen was added over 5 minutes 38.9 ml (0.0389 mol) of 1M lithium trisiamylborohydride in tetrahydrofuran. The reaction was stirred for 10 minutes and then warmed to room temperature. Saturated sodium bicarbonate solution (36.9 ml) was added followed by 30% hydrogen peroxide (14.19 ml, 0.138 mol) which was added slowly while maintaining the temperature at 30° using an ice bath. The reaction was diluted with water (120 ml) and extracted with ethyl acetate (400 ml). The organic layer was washed with water (100 ml), dried over sodium sulfate, and concentrated in vacuo to give 17.8 g of the crude desired product as a residue containing no detectable (1α, 2β, 3α)-3-hydroxy-1,2-cyclobutanedimethanol, 1,2-dibenzoate ester. The residue was purified by preparative high pressure liquid chromatography on two Waters Prep 500 silica gel columns eluting with 30% ethyl acetate in hexane to give 9.17 g of (1α, 2β, 3α)-3-hydroxy-1,2-cyclobutanedimethanol, 1,2-dibenzoate ester.

Alternatively the crude product (42g) obtained from the reduction of 40.5g (0.12 mol) of (trans)-2,3-bis-[(benzoyloxy)methyl]cyclobutanone with 120 ml (0.12 mol) of 1M lithium trisiamylborohydride (as above) was dissolved in 100 ml of hexane/ethyl acetate (2/1) and applied to a dry pad of 1.2 L of Merck silica gel-60. The pad was washed with 5L of the same solvent mixture, taking 500 ml fractions. The product containing fractions were combined and evaporated to give 39.8 g of the desired material as a colorless liquid, pure enough for use in the next step of the synthesis.

G) (1α, 2β, 3α)-3-[[(4-Methylphenyl)sulfonyl]oxy]-1,2-cyclobutanedimethanol, dibenzoate ester.

To a solution of (1α, 2β, 3α)-3-hydroxy-1,2-cyclobutanedimethanol, 1,2-dibenzoate ester (7.31 g, 0.0215 mol), previously dried by concentrating it from dry pyridine (2×20 ml), in 36 ml of dry pyridine was added p-toluenesulfonyl chloride (6.56 g, 0.0344 mol). The reaction was stirred for 16 hours at 60° under nitrogen, and the pyridine was removed in vacuo. Residual pyridine was removed by co-distillation with toluene (2×30 ml). The residue was dissolved in ethyl acetate (480 ml) and washed with saturated potassium carbonate. The organic layer was dried over sodium sulfate, filtered and concentrated in vacuo to a residue which was purified by chromatography on Merck silical gel-60 (1500 ml). The column was eluted with a forerun of 3000 ml of ethyl acetate:hexane (1:5).

The column was then eluted with ethyl acetate:hexane (1:3) collecting 50 ml fractions. The appropriate fractions were combined and concentrated to give 7.00 g of (1α, 2β, 3α)-3[[(4-methylphenyl)sulfonyl]oxy]-1,2-cyclobutanedimethanol, dibenzoate ester.

Alternatively, after heating (1α, 2β, 3α)-3-hydroxy-1,2-cyclobutanedimethanol, 1,2-dibenzoate ester (39.8 g, 117 mmol) with p-toluenesulfonyl chloride (24.65g, 128.5 mmol) in 60 ml of pyridine at 60° C. for 22 hours, the temperature was lowered to 40° C. and 2 ml of water was added. After 2 hours, the volatiles were removed and the residue was partitioned between ethyl acetate and water. The organic layer was washed with 3% sodium bicarbonate and dried over sodium sulfate. The crude material obtained on concentration of the solvent was triturated with pentane to give 39.4 g of crude product. This material was dissolved in 120 ml of ethyl acetate with gentle warming. The solution was cooled to room temperature and diluted with 120 ml of pentane. Standing for several hours at +5° C. gave crystals which were filtered and dried to give 32.6g of the pure desired product.

Alternate preparation of (1α, 2β, 3α)-3-[[(4-Methylphenyl)sulfonyl]-oxy]-1,2-cyclobutanedimethanol dibenzoate ester.

To a solution of (1α, 2β, 3α)-3-hydroxy-1,2-cyclobutanedimethanol, dibenzoate ester (3.096 g, 9.10 mmol) in dry toluene (25 ml) was added p-toluensulfonic acid monohydrate (2.08 g, 10.9 mmol), triethylamine (1.51 ml, 10.9 mmol), triphenylphosphine (3.81 g, 14.6 mmol) and diisopropyl azodicarboxylate (2.87 ml, 14.6 mmol). The reaction was heated at 80° under nitrogen. Additional triphenylphosphine (1.90 g, 7.3 mmol) and diisopropyl azodicarboxylate (1.43 ml, 7.3 mmol) were added after 1 hour and again after 3 hours. After another 3 hours of heating, additional triphenylphosphine (0.95 g, 3.65 mmol) and diisopropyl azodicarboxylate (0.717 ml, 3.65 mmol) were added. The reaction was heated for an additional hour, cooled to room temperature and filtered. The precipitate was washed with toluene (20 ml), and the filtrate and wash were combined and concentrated in vacuo to a residue which was dissolved in ethyl acetate (100 ml). The ethyl acetate solution was washed with water (2×30 ml), dried over sodium sulfate, filtered and concentrated in vacuo. The residue was purified by chromatography on Merck silica gel-60 (300 ml) using hexane:ethyl acetate (5:1), and the appropriate fractions were combined and concentrated to 20 ml. This concentrate was diluted with 30 ml of hexane and allowed to stand at room temperature overnight. The crystals were collected by filtration, washed with hexane and dried to give 2.18 g (batch 1) of pure desired product.

The mother liquors from batch 1 were concentrated to 40 ml and left at room temperature overnight. The crystals (batch 2) were collected by filtration, dried in vacuo, and chromatographed on Merck silica gel-60 (300 ml) using 2% ethyl acetate in toluene to give 1.02 g (batch 3) of still impure desired product. The mother liquors from batch 2 were chromatographed on Merck silica gel-60 (300 ml) using 2% ethyl acetate in toluene to give 187 mg (batch 4) of still impure desired product. Batches 3 and 4 were combined, and recrystallized from hexane:ethyl acetate to give an additional 770 mg of pure desired product. The total yield of pure desired product was 2.95g.

H) (1α, 2β, 3α)-3-[2-Amino-6-(phenylmethoxy)-9H-purin-9-yl]-1,2-cyclobutanedi methanol, 1,2-dibenzoate ester.

To a solution of (1α, 2β, 3α)-3-[[(4-methylphenyl)sulfonyl]oxy]-1,2-cyclobutanedimethanol, dibenzoate (1.072 g, 2.17 mmol) in dimethylformamide (20 ml) was added 2-amino-6-(phenylmethoxy)-9H-purine (784 mg, 3.25 mmol), 18-crown-6 (573 mg, 2.17 mmol) and potassium carbonate (600 mg, 4.34 mmol). The reaction was stirred under nitrogen at 110° for 24 hours. The solvents were removed in vacuo, and the residue was chromatographed on column of Merck silica gel-60 (2.5×20 cm) using ethyl acetate:hexane (3:1) to give 400 mg of pure desired product. Other fractions that contained impure desired product were combined and rechromatographed on Merck silica gel-60 (1.5×30 cm) using ethyl acetate hexane (2:1) to give 52 mg of additional desired product, yielding a total of 452 mg of desired product.

I) (1α, 2β, 3α)-3-[2-Amino-6-(phenylmethoxy)-9H-purin-9-yl]-1,2-cyclobutanedi methanol To a solution of (1α, 2β, 3α)-3-[2-amino-6-(phenylmethoxy)-9H-purin-9-yl]-1,2-cyclobutanedimethanol, 1,2-dibenzoate ester (452 mg, 0.803 mmol) in dry methanol (12 ml) was added a 25% solution of sodium methoxide in methanol (109 µl 0.482 mmol). The reaction was stirred under nitrogen at 40° for 1 hour. The solvent was removed in vacuo and water (10 ml) was added. The pH was lowered to 7 with 1N HCl. The solvents were removed in vacuo and the residue was triturated with ether (2×20 ml) and dried to give 358 mg of crude desired product, which was then used in the next step.

J) (1α, 2β, 3α)-9-[2,3-Bis(hydroxymethyl)cyclobutyl]guanine

To a suspension of (1α, 2β, 3α)-3-[2-amino-6-(phenylmethoxy)-9H-purin-9-yl]-1,2-cyclobutanedimethanol (358 mg, 1.0 mmol) in methanol (5 ml) was added 3N HCl (2.5 ml). The reaction was stirred for 4 hours at 45°. The solvents were removed in vacuo, and the residue was dissolved in water (20 ml). The pH was raised to 7 with 1N KOH. A 10% aliquot was taken, and the solvents were removed n vacuo. The residue was concentrated from methanol (3×4 ml) and ethyl acetate (2×4 ml). The residue was dissolved in water (4 ml) with heating and applied to a column of CHP-20P resin 1.1×20 cm; Mitsubishi Chemical Industries Ltd. (75–150 micron)]. Elution with water, 2% acetonitrile/water, and 4% acetonitrile/water gave 11 mg of desired product.

The remaining 90% of the reaction was concentrated in vacuo and then concentrated from methanol (3×20 ml) and ethyl acetate (2×20 ml). The residue was dissolved in water (30 ml) with heating and applied to a column of CHP-20P resin (2.5×15 cm). Elution with water, 2% acetonitrile/water, 4% acetonitrile/water and 10% acetonitrile/water gave 111 mg of additional (1α, 2β, 3α)-9-[2,3-bis(hydroxymethyl)cyclobutyl]guanine having m.p. >220°.

Calculated for $C_{11}H_{15}N_5O_3.1.43H_2O$: C. 45.40; H. 6.18; N. 24.08; $H_2O$, 8.83.

Found:C, 45.66; H, 5.95; N, 23.82, $H_2O$, 8.83.

EXAMPLE 2

(1α, 2β, 3α)-3-(6-Amino-9H-purin-9-yl)-1,2-cyclobutanedimethanol

A) (1α, 2β, 3α)-3-(6-Amino-9H-purin-9-yl)-1,2cyclobutanedimethanol, dibenzoate ester.

To a solution of (1α, 2β, 3α)-3-[[(4-methylphenyl)sulfonyl]oxy]-1,2-cyclobutanedimethanol dibenzoate ester (988 mg, 2 mmol) in dry dimethylformamide (20 ml) under nitrogen was added adenine (405 mg, 3 mmol), 18-crown-6 (538 mg, 2 mmol), and potassium carbonate (276 mg, 2 mmol). The reaction was heated at 110° for 16 hours, and then the solvent was removed in vacuo to give a residue, which was purified by column chromatography on Merck silica gel-60 (400 ml). Elution with 0.1%, 0.5%, 5% and 10% methanol in ethyl acetate gave 522 mg of still impure product. Column chromatography of this material on Merck silica gel-60 (400 ml) using dichloromethane-methanol (20:1) afforded 400 mg of pure (1α, 2β, 3α)-3-(6-amino-9H-purin-9-yl)-1,2-cyclobutanedimethanol, dibenzoate ester.

B) (1α, 2β, 3α)-3-(6-Amino-9H-purin-9-yl)-1,2-cyclobutanedimethanol.

To a suspension of (1α, 2β, 3α)-3-(6-amino-9H-purin-9-yl)-1,2-cyclobutanedimethanol, dibenzoate ester (400 mg, 0.899 mmol) in dry methanol (20 ml) was added a 25% solution of sodium methoxide in methanol (123 μl, 0.539 mmol). The mixture was stirred at 40° for 45 minutes, and then the solvent was removed in vacuo. The residue was slurried in water (20 ml), the pH was adjusted to 7.0 using 1N HCl, and the volatiles were removed. The residue was purified by column chromatography on CHP-20P resin. Elution with water, a gradient of 0 to 20% methanol in water and then 20% and 30% methanol in water afforded 128 mg of (1α, 2β, 3α)-3-(6-amino-9H-purin-9-yl)-1,,2-cyclobutanedimethanol as a solid having m.p. 181–183°.

Calculated for $C_{11}H_{15}N_5O_2.0.1 H_2O$: C,52.63; H,6.10; N,27.90 Found:C,52.64; H.6.10; N,28.00

EXAMPLE 3

(1α, 2β, 3α)-1-[2,3-Bis(hydroxymethyl)cyclobutyl]-5-methyl-2,4(1H,3H)-pyrimidinedione A) (1α, 2β, 3α)-1-[2,3-Bis[(benzoyloxy)methyl]cyclobutyl]-5-methyl-2,4(1H,3H) -pyrimidinedione.

A mixture of (1α, 2β, 3α)-3[[(4-methylphenyl)-sulfonyl]oxy]-1,2-cyclobutanedimethanol, dibenzoate ester, (1.245 g, 2.52 mmol), thymine (625 mg, 4.96 mmol), potassium carbonate (1.39 g, 10.1 mmol) and 18-crown-6 (664 mg, 2.51 mmol) in dry dimethylformamide (12.5 ml) under argon was heated with stirring at 105° for 16 hours and then at 125° for 1 hour. Additional thymine (310 mg, 2.2 mmol) and potassium carbonate (354 mg, 2.6 mmol) were added, and heating at 125° was continued for 2 hours. The reaction mixture was cooled and filtered, and the insolubles were washed with dimethylformamide. The dimethylformamide filtrates were combined and evaporated to a residue, which was triturated with ethyl acetate. The solids were removed by filtration, and the filtrate was evaporated to a residue. This residue was dissolved in a small volume of ethyl acetate-hexane (ca. 1:1) and applied to a column of Merck silica gel-60 (5×11.5 cm) packed in hexane. Elution with ethyl acetate-hexane (4:1) and then ethyl acetate gave 219 mg of partially purified desired product. Chromatography of this material on a column of Merck silica gel-60 (packed in dichloromethane) by elution with 10%, 20%, 30% and 50% ethyl acetate in dichloromethane afforded 166 mg of pure (1α, 2β, 3α)-1-[2,2-bis[benzoyloxy)methyl]cyclobutyl]-5-methyl-2,4(1H,3H) -pyrimidinedione as a white solid.

B) (1α, 2β, 3α)-1-[2,3-Bis(hydroxymethyl)cyclo-butyl]-5-methyl-2,4(1H,3H) -pyrimidinedione A 25% solution of sodium methoxide in methanol (44.7 μl, 0.196 mmol) was added to a stirred suspension of (1α, 2β, 3α)-1-[2,3-bis[(benzoyloxy)methyl]cyclobutyl]-5-methyl-2,4(1H,3H)-pyrimidinedione (146 mg, 0.326 mmol) in dry methanol (4.9 ml) under argon at 40°. After 4 hours, the clear solution was cooled to room temperature and concentrated in vacuo to a residue, which was taken up in water. The pH was adjusted to 7 using dilute hydrochloric acid, and the solution was applied to a column (1.5×21 cm) of CHP-20P resin packed in water. Elution with water, 2%, 4% and 10% acetonitrile in water afforded, after evaporation and subsequent lyophilization from water, 58 mg of (1α, 2β, 3α)-1-[2,3bis(hydroxymethyl)cyclobutyl]-5-methyl-2,4(1H,3H)-pyrimidinedione as a deliquescent solid. Proton NMR (270 MHz,

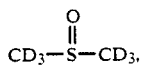

tetramethylsilane) δ: 11.11 (broad singlet, 1H), 7.64 (doublet, J=1.1Hz, 1H), 4.56 (multiplet, 2H), 4.47 (multiplet, 2H), 4.47 (multiplet, 1H), 3.44 (multiplet, 4H), 2.5 (multiplet,

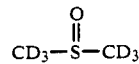

solvent+1H), 1.85 (multiplet, 1H), 1.84 (multiplet, 1H), 1.79 (doublet, J =1.1Hz, 3H).

EXAMPLE 4

(1α, 2β, 3α)-4-Amino-1-[2,3-bis(hydroxymethyl)-cyclobutyl]-2(1H)-pyrimidinone

A) (1α, 2β, 3α)-4-Amino-1-[2,3-bis[(benzoyloxy)methyl]cyclobutyl]-2(1H)-pyrimidinone.

A mixture of (1α, 2β, 3α)-3-[[(4-methylphenyl)sulfonyl)-sulfonyl]oxy]-1,2-cyclobutanedimethanol, dibenzoate ester (1.51 g, 3.05 mmol), cytosine (678 mg, 6.10 mmol), potassium carbonate (1.69 g, 12.2 mmol) and 18-crown-6 (804 mg, 3.04 mmol) in 12.5 ml of dry dimethyl sulfoxide was stirred under argon at 112° for 4.5 hours. The reaction mixture was cooled to room temperature and neutralized by the addition of glacial acetic acid (0.7 ml, 12.2 mmol). Solvent was removed in vacuo, and the residue was taken up in ethyl acetate. Solid material was removed by filtration, and the filter cake was washed with ethyl acetate. The ethyl acetate filtrate was concentrated to a residue, which was dissolved in toluene and applied to a column of Merck silica gel (2.5×28.5 cm) packed in toluene. Elution with isopropanol in toluene afforded 156 mg of the desired product.

B) (1α, 2β, 3α)-4-Amino-1-[2,3-bis(hydroxymethyl)cyclobutyl]-2(1H)-pyrimidinone

A 25% solution of sodium methoxide in methanol (48 μl, 0.209 mmol) was added to a solution of (1α, 2β, 3α)-4-amino-1-[2,3-bis[(benzoyloxy)methyl]cyclobutyl]-2(1H) -pyrimidinone (151.3 mg, 0.349 mmol) in 5.25 ml of dry methanol. The reaction was stirred at 40° for 75 minutes and cooled to room temperature. The solvent was removed in vacuo, and the residue was dissolved in water. The pH was adjusted to 7.05 with 1N HCl. The aqueous solution was loaded onto a column of CHP-20P resin packed in water, and the column was flushed with 50 ml of water and then eluted with a continuous gradient of 0–50% acetonitrile in water. Combination of the appropriate fractions and removal of solvent in vacuo afforded the desired product as a transparent glass (52 mg).
Proton NMR (270 MHz,

tetramethylsilane) δ: 7.69 (doublet, J=7Hz, 1H), 6.98 (broad singlet, 2H), 5.71 (doublet, J=7.6Hz, 1H), 4.65 (broad multiplet, 2H), 4.37 (multiplet, 1H), 3.43 (multiplet, 4H), 2.43 (multiplet, 1H), 2.31 (multiplet, 1H), 2.20 (multiplet, 1H), 1.77 (multiplet, 1H).

EXMAPLE 5

[1α, 2β,3α]-1-[2,3-Bis(hydroxymethyl)-cyclobutyl]-5-(2-bromoethenyl)-2,4(1H, 3H)-pyrimidinedione A) (1α, 2β, 3α)-1-[2,3-Bis[(benzoyloxy)methyl]cyclobutyl]-2,4(1H,3H)-pyrimidinedione.

To a solution of uracil (1.26 g, 11.23 mmol, dried at 50° for 16 hours) and 18-crown-6 (1.98 g, 7.49 mmol) in dimethylsulfoxide (9 ml) at 50° was added potassium carbonate (2.07 g, 14.98 mmol) and (1α, 2β, 3α)-3-[[(4-methylphenyl)sulfonyl]oxy]-1,2-cyclobutanedimethanol, dibenzoate ester (3.7 g, 7.49 mmol). Upon heating to 100° under nitrogen, an emulsion formed. Additional dimethylsulfoxide (3 ml) was added, and the reaction was stirred at 100° for 24 hours. The solvents were removed in vacuo to give a residue, which was purified by chromatography on Merck silica gel-60 (700 ml) using a gradient of toluene to 3% isopropyl alcohol in toluene. The appropriate fractions were combined to give 850 mg of pure desired product. Fractions containing impure desired product were combined and concentrated to a residue, which was dissolved in toluene (1 ml). The crystals that formed were collected and dried to give 35 mg of additional pure desired product.

B) (1α, 2β, 3α)-1-[2,3-Bishydroxymethyl)-cyclobutyl]-2,4(1H,3H)-pyrimidinedione.

To a suspension of (1α, 2β, 3α)-1-[2,3-bis [(benzoyloxy)methyl]cyclobutyl]-2,4(1H,3H)pyrimidinedione (885 mg, 2.04 mmol) in dry methanol (25 ml) was added a 25% solution of sodium methoxide in methanol (264μl, 1.22 mmol). The reaction was heated to 40° for 3 hours under nitrogen. The solvents were removed in vacuo, and the residue was dissolved in water (5 ml). The pH was lowered to 7 with 1N HCl, and the solution was stored overnight at 0°. The resulting precipitate and supernatant were purified on a single CHP-20P resin column (200 ml) using a step gradient of water, 2% acetonitrile/water and 4% acetonitrile/water, to give 423 mg of desired product.

C) (1α, 2β, 3α)-1-[2,3-Bis[hydroxymethyl)cyclobutyl]-5-iodo-2,4(1H,3H) -pyrimidinedione.

To a suspension of (1α, 2β, 3α)-1-[2,3-bis(hydroxymethyl)cyclobutyl]-2,4(1H,3H) -pyrimidinedione (423 mg, 1.87 mmol) in dioxane (38 ml, purified on basic alumina) was added iodine (950 mg, 3.74 mmol) and 0.8M nitric acid (2.5 ml, 2 mmol). This solution was stirred at 95° for 90 minutes and cooled to room temperature. A solution of saturated aqueous sodium thiosulfate was added until the dark red color faded. The reaction was concentrated in vacuo to give a slightly yellow residue. This material was purified by chromatography on CHP-20P resin (150 ml) using a gradient of water to 50% acetonitrile in water to give 557 mg of desired product.

D) [1α, 2β, 3α]-3-[1-[2,3-Bis(hydroxymethyl)cyclobutyl]-1,2,3,4-tetrahydro-2,4-dioxo-5-pyrimidinyl]-2-propenoic acid, methyl ester.

A suspension of palladium(II)acetate (17.5 mg, 0.078 mmol), triphenylphosphine (40.9 mg, 0.15 mmol) and triethylamine (290 μl, 2.08 mmol) in dioxane (20 ml, purified on basic alumina) was heated for 15 minutes at 85° under nitrogen, and then a solution of (1α, 2β, 3α)-1-[2,3-bis(hydroxymethyl)cyclobutyl]-5-iodo-2,4(1H,3H)-pyrimidine (457 mg, 1.3 mmol) and methyl acrylate (468 μl, 5.2 mmol) in dioxane (10 ml) was added. The reaction was heated at 85° under nitrogen. After 4 hours, additional methyl acrylate (234 μl, 2.7 mmol) was added. After heating for an additional 2 hours, the reaction was still not complete. Celite (300 mg) was added, and the warm reaction was filtered. The solvents were removed in vacuo. The residue was dried by concentrating it from dry dioxane (2×10 ml) and the residue was then submitted to the following reaction conditions.

The reaction was repeated, but this time the oxygen was removed from the dioxane by bubbling argon through the solvent. After heating a suspension of palladium(II) acetate (17.5 mg, 0.078 mmol), triphenylphosphine (40.9 mg, 0.15 mmol), and triethylamine (290 μl, 2.08 mmol) in dioxane (20 ml) for 15 minutes at 85° under nitrogen, a solution of the above residue and methyl acrylate (468 μl, 5.2 mmol) in dioxane (10 ml) was added. The reaction was heated for 3 hours at 85°. Celite (300 mg) was added and the warm reaction was filtered, cooled to room temperature, and concentrated in vacuo. The residue was applied to a column of Merck silica gel-60 (150 ml, packed in chloroform) and purified using a step gradient from chlorform to 5%, 7.5% and 10% methanol/chloroform. The appropriate fractions were combined and concentrated to give 310 mg of desired product contaminated with triethylammonium salts. This mixture was dissolved in water (5 ml) and ethyl acetate (50 ml). The layers were separated and the water layer was extracted with ethyl acetate (4×30 ml). The ethyl acetate layers were combined, dried over sodium sulfate, filtered and concentrated to give 230 mg of the desired product.

E)[1α, 2β, 3α]-3-[1-[2,3-Bis(hydroxymethyl)-cyclobutyl]-1,2,3,4-tetrahydro-2,4-dioxo-5-pyrimidinyl-2-propenoic acid.

A solution of [1α, 2β, 3α]-3-[1-[2,3-bis(hydroxymethyl)cyclobutyl]-1,2,3,4-tetrahydro-2,4-dioxo-5-pyrimidinyl]-2-propenoic acid, methyl ester (230 mg, 0.742 mmol) in 2M sodium hydroxide (3.7 ml, 7.42 mmol) was stirred at room temperature for 1.5 hours, and the reaction was cooled to 4°. The pH was lowered to 2 with 6N HCl, and the reaction was allowed to stand for 1 hour at 4°. The precipitate was collected by filtration, washed with water and dried over $P_2O_5$ in vacuo for 16 hours to give 120 mg of desired product. The mother liquors and wash were concentrated to 3 ml and allowed to stand at 4° for 16 hours. The crystals were collected, washed with water, dried over $P_2O_5$ in vacuo for 4 hours to give 7 mg of additional desired product.

F) [1α, 2β, 3α]-1-[2,3-Bis(hydroxymethyl)cyclobutyl]-5(2-bromoethenyl)-2,4(1H, 3H)-pyrimidine-dione.

To a solution of [1α, 2β, 3α]-3-[1-[2,3-bis(hydroxymethyl)cyclobutyl]-1,2,3,4-tetrahydro-2,4-dioxo-5-pyrimidinyl]-2-propenoic acid (127 mg, 0.429 mmol, dried by evaporation of dimethylformamide, 2 ×3 ml) in dimethylformamide (2 ml) was added potassium bicarbonate (129 mg, 1.29 mmol). A solution of N-bromosuccinimide (76 mg, 0.429 mmol) in dimethylformamide (1 ml) was added, and the reaction was stirred at room temperature for 2.5 hours. The reaction was filtered and concentrated in vacuo. The residue was concentrated from water (2×5 ml), and then chromatographed on CHP 20P resin (110 ml) using a gradient of water to 30% acetonitrile in water to give, after concentration in vacuo, 99 mg of [1α, 2β, 3α]-1-[2,3-bis(hydroxymethyl)cyclobutyl]-5(2-bromoethenyl) -2,4(1H, 3H)-pyrimidinedione having m.p. 155-157°.

Calculated for $C_{12}H_{15}N_2O_4Br.0.31\ H_2O$ C, 42.7g; H,4.68; N,8.32 Found: C, 42.85; H,4.69; N,8.26

EXAMPLE 6

(1α, 2β, 3α)-2-Amino-9-[2,3-bis(hydroxymethyl)cyclobutyl]-8-bromo-1,9,dihydro-6H -purine-6-one.

To a stirred suspension of (1α, 2β, 3α)-9[2,3-bis(hydroxymethyl)cyclobutyl]guanine (72 mg, 0.272 mmol) in water (9 ml) was added 0.5 ml of a saturated bromine-water solution. Additional bromine-water solution (0.5 ml) was added after 25 minutes and again after 50 minutes. After 15 minutes of additional stirring, the precipitated material was filtered, washed with water, slurried in water (3 ml), and applied to a CHP-20P column (24 ml) packed in water. Elution with a step gradient of water, 4% acetonitrile/water, and 8% acetonitrile/water gave 45 mg of desired product. This material was combined with 49 mg of desired product from a similar reaction run on the same scale, and the combined products were crystallized from water (7 ml) to give 74 mg of (1α, 2β, 3α)-2-amino9-[2,3-bis(hydroxymethyl)cyclobutyl]-8-bromo-1,9,dihydro-6H-purin-6-one having m.p. 130°. NMR (270 MHz,

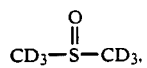

tetramethylsilane)δ: 10.67 (broad singlet, 1H), 6.43 (broad singlet, 2H), 4.59 (quartet, J=9Hz,1H), 4.55 (triplet, J=5Hz,1H), 4.48 (triplet, J=5Hz, 1H), 3.59 (triplet, J=6Hz, 2H), 3.44 (triplet, J=5Hz, 2H), 2.56 (multiplet, 2H), 2.26 (multiplet, 1H), 2.21 (multiplet, 1H).

EXAMPLE 7

(1α, 2β, 3α)-1-[2,3-Bis(hydroxymethyl)cyclobutyl]-5-iodo-2,4(1H,3H)-pyrimidinedione.

A) (1α, 2β, 3α)-1-[2,3-Bis(benzoyloxy)methyl]cyclobutyl]-2,4(1H,3H)-pyrimidinedione.

A mixture of (1α, 2β, 3α)-3-[[(4-methylphenyl)sulfonyl]oxy]-1,2-cyclobutanedimethanol, dibenzoate ester (1.25 g, 5.07 mmol), uracil (0.567 g, 5.07 mmol), potassium carbonate (1.40 g, 10.2 mmol) and 18-crown-6 (670 mg, 2.54 mmol) in dry DMSO (12.5 ml) was heated at 110° for 4.5 hours. The solvent was removed in vacuo and the resulting semi-solid was triturated twice with ethyl acetate. The combined ethyl acetate supernatants were concentrated to a small volume, diluted with an equal volume of hexane and applied to a column of Merck silica gel-60 (2.5×25 cm) packed in hexane. The column was eluted with ethyl acetate-hexane (1:4) and (1:1) and then ethyl acetate to afford partially purified desired product (250 mg). Chromatography of this material on a silical gel column (1.5×24.5 cm) packed in methylene chloride, eluting with ethyl acetatemethylene chloride (1:4) and (1:1) and then ethyl acetate failed to resolve the impurities. Subsequent chromatography on a silica gel column (1.5×25 cm) packed in toluene and eluting with isopropanol-toluene (4:96) afforded the pure desired product (56.5 mg) as well as impure desired product. Recrystallizaiton of the impure material from toluene afforded additional pure desired product (86.3 mg; giving a total yield of 143 mg).

B) (1α, 2β, 3α)-1-[2,3-Bis(hydroxymethyl)cyclo-butyl]-2,4(1H,3H)-pyrimidinedione.

A mixture of (1α, 2β, 3α)-1-[2,3-bis(benzoyloxy)methyl]cyclobutyl]-2,4(1H,3H) -pyrimidinedione (142.9 mg, 0.329 mmol), 45 μl of a 25% solution of sodium methoxide in methanol, and 4.9 ml of dry methanol was stirred at 40° under argon for 8.5 hours. The reaction was cooled to room temperature, and the solvent was removed in vacuo. The sticky residue was partially dissolved in a few milliliters of water and the pH was adjusted to 7.00 with dilute hydrochloric acid and sodium bicarbonate. This solution (7-8 ml) was applied to a column of CHP-20P resin (1.5×23.5 cm) packed in water. After elution with water (ca. 50 ml), the column was eluted with aqueous acetonitrile (2%, 4% and 10%) to give 55.8 mg of desired product as a white solid.

C) (1α, 2β, 3α)-1-[2,3-Bis(hydroxymethyl)cyclobutyl]-5-iodo-2,4(1H,3H) -pyrimidinedione.

A solution of (1α, 2β, 3α)-1-[2,3-bis-(hydroxymethyl)cyclobutyl]-2,4(1H,3H) -pyrimidinedione (54.7 mg, 0.242 mmol), iodine (123 mg, 0.484 mmol), and aqueous nitric acid (0.8 N, 0.256 mmol) in 5 ml of dioxane was stirred at 105° for 85 minutes. After cooling to room temperature, the mixture was decolorized with aqueous sodium thiosulfate and concentrated in vacuo to a solid. The solid was taken up in water and concentrated in vacuo (3 times). The resultant solid was partially dissolved in water and applied to a column of CHP-20P resin (1.5×20 cm) packed in water. After elution with water (ca. 50 ml), the column was eluted with a continuous gradient from water to 50% acetonitrile in water to give 67.3 mg of (1α, 2β, 3α)-1-[2,3-bis(hydroxymethyl)cyclobutyl]5-iodo-2,4(1H,3H) -pyrimidinedione as a white solid having m.p. 170-171°.

Calculated for $C_{10}H_{13}IN_2O_4 \cdot 0.27 H_2O$: C, 33.65; H, 3.82; N, 7.85. Found: C, 33.68; H, 3.77; N, 7.82

EXAMPLE 8

(1α, 2β, 3α)-5-Amino-3-[2,3-bis(hydroxymethyl)cyclobutyl]-3,6-dihydro-7H -1,2,3-triazolo[4,5-d]-pyrimidin-7-one

A) 4-Chlorobenzenediazonium chloride.

To a suspension of 4-chloroaniline (21.14 g, 0.166 mol) in water (156 ml) and 12N HCl (46 ml) at 0° was added sodium nitrite (12.62 g, 0.182 mol) in water (156 ml) over 20 minutes keeping the reaction temperature below 10°. The solution of 4-chlorobenzenediazonium chloride was filtered, kept at 0° for 30 minutes and then used in the next step.

B) 6-Chloro-5-[(4-chlorophenyl)azo]-2,4-pyrimidinediamine.

To a suspens-ion of 4-chloro-2,6-diaminopyrimidine (21.68 g, 0.150 mol) in water (750 ml) and acetic acid (750 ml) was added sodium acetate (300 g). Solution occurred after stirring for 20 minutes, and then the solution of 4-chlorobenzenediazonium chloride (0.166 mol) was added with cooling over 30 minutes at a rate that kept the reaction at 18°. The reacton was stirred overnight at room temperature, and the orange crystals were filtered, washed with water (4×400 ml), and dried in vacuo to give 17.6 g of 6-chloro-5-[(4-chlorophenyl)azo]-2,4-pyrimidinediamine. The mother liquors were cooled to 5° for 20 hours, and the crystals were collected and dried in vacuo to give 6.94 g of additional 6-chloro-5-[(4-chlorophenyl)azo]-2,4-pyrimidineadiamine.

C) 6-Chloro-2,4,5-pyrimidinetriamine

A suspension of 6-chloro-5-[(4-chlorophenyl)azo]-2,4-pyrimidinediamine (24.55 g, 0.0906 mol) in ethanol (640 ml), water (640 ml) and acetic acid (64 ml) was heated to 70° under nitrogen. Zinc dust (75 g) was added slowly over 1 hour, and then the reaction was stirred an additional hour at 70°. Then the reaction was cooled to room temperature and filtered under nitrogen. The filtrate was cooled to 0° and the pH was raised to 10 with 10% sodium hydroxide (400 ml). The precipitated zinc hydroxide was removed by filtration through Celite, and the dark red filtrate was neutralized to pH 7 with glacial acetic acid and concentrated to 300 ml. Water (50 ml) was added, the reaction was cooled to 0°, and the pH raised to 9 with 10% NaOH. The solution was allowed to stand at 5° for 3 days. The crystals were collected, washed with water (50 ml) and then ether (50 ml), and dried at 35° for 16 hours in vacuo to give 10.94 g of desired product.

D) 7-Chloro-1H-1,2,3-triazolo[4,5-d]pyrimidin5-amine.

A solution of 6-chloro-2,4,5-pyrimidinetriamine (10.94 g, 0.0686 mol) and isoamyl nitrite (9.20 ml, 0.0686 mol)in dioxane (500 ml, freshly purified by passage through basic alumina) was heated under nitrogen with stirring for 2 hours at 90°. The reaction mixture was cooled, treated with activated carbon, filtered, and concentrated to 150 ml. Petroleum ether (250 ml, bp 35-60°) was added. The precipitate was filtered, washed the petroleum ether (50 ml) and dried in vacuo over $P_2O_5$ at 40° for 16 hours to give 9.23 g of crude desired product which was then used in the next step.

E) 7-(Phenylmethoxy)-1H-1,2,3-triazolo[4,5-d]pyrimidin-5-amine.

Sodium metal (3.7 g, 0.162 mol) was added in pieces to benzyl alcohol (117 ml, 1.13 mol) under nitrogen over 20 minutes. The reaction was then heated to 80° for 90 minutes. All of the sodium metal dissolved, and the reaction was left at room temperature for 16 hours. 7-Chloro-1H-1,2,3triazolo[4,5-d]pyrimidin-5-amine (9.23 g. 0.0541 mol) was then added, and the reaction was heated to 60° for 5 hours. The reaction was cooled and left at 5° for 16 hours. Water (500 ml) was added to dissolve the precipitate and then the mixture was extracted with ether (3×200 ml). The pH of the water layer was lowered to 7.0 with concentrated HCl and then to 5.5 with 1N HCl. The precipitate was filtered and dried at room temperature over $P_2O_5$ in vacuo to give 8.05 g of desired product.

F) (1α, 2β, 3α)-3-[5-Amino-7(phenylmethoxy)-3H-1,2,3-triazolo[4,5-d]-pyrimidin-3-yl]-1,2-cyclobutanedimethanol, dibenzoate ester To a suspension of 60% NaH (78 mg, 1.96 mmol) in dimethylformamide (4 ml) under nitrogen was added 7-(phenymethoxy)-1H-1,2,3-triazolo[4,5-d]pyrimidin-5-amine (474 mg, 1.96 mmol). After 10 minutes, (1α, 2β, 3α)-3-[[(4-methylphenyl) sulfonyl]oxy]-1,2-cyclobutanedimethanol, dibe ester (880 mg, 1.78 mmol) was added, and the reaction was heated at 85° for 24 hours. The solvents were removed in vacuo and the residue was triturated with ethyl acetate (3×30 ml) and filtered. The ethyl acetate extracts were combined and concentrated to a residue, which was purified on Merck silica gel-60 (100 ml), eluting with a stepwise gradient of 10% ethyl acetate in hexane to 100% ethyl acetate. The desired product eluted with 50% ethyl acetate in hexane to afford 205 mg of (1α, 2β, 3α)-3-[5-amino-7-(phenylmethoxy)-3H1,2,3-triazolo[4,5-d]-pyrimidin-3-yl]-1,2-cyclobutanedimethanol, dibenzoate ester.

G) (1α, 2β, 3α)-3-[5-Amino-7-(phenylmethoxy)-3H-1,2,3-triazolo[4,5-d]-pyrimidin-3-yl]-1,2-cyclobutanedimethanol To a solution of (1α, 2β, 3α)-3-[5-amino-7-(phenylmethoxy)-3H-1,2,3-triazolo[4,5-d]-pyrimidin-3-yl]-1,2-cyclobutanedimethanol, dibenzoate ester (205 mg, 0.363 mmol) in dry methanol (6 ml) was added a 25% solution of sodium methoxide in methanol (50µl, 0.218 mmol). This was heated to 40° under nitrogen for 1 hour, and then water (2 ml) was added and the pH was adjusted to 7 with 1M HCl. The reaction was concentrated in vacuo to give crude desired product.

H) (1α, 2β, 3α)-5-Amino-3-[2,3-bis(hydroxymethyl)cyclobutyl]-3,6-dihydro-7H-1,2,3-triazolo[4,5-d]pyrimidin-7-one.

Crude (1α, 2β, 3α)-3-[5-amino-7-(phenylmethoxy)-3H-1,2,3-triazolo[4,5-d]-pyrimidin-3-yl]-1,2-cyclobutanedimethanol from above was slurried in 1.5 ml of methanol and then 3N HCl (600 µl) was added. The reaction was heated to 45° for 4 hours, and left at room temperature for 16 hours. The pH was raised to 7 with 1N KOH, and the solution was concentrated in vacuo to a residue. Chromatography of this residue on CHP-20P resin (34 ml) using a gradient of water to 70% acetonitrile in water gave 64 mg of (1α, 2β, 3α)-5-amino-3-[2,3-bis(hydroxymethyl)cyclobutyl]-3,6-dihydro-7H-1,2-tiazolo[4,5-d]-pyrimidin-7-one having m.p.>200°.

Calculated for $C_{10}H_{14}N_6O_3 \cdot 2.5H_2O$: C,38.57;H,6.15;N,26.99. Found: C,39.17;H,4.98;N,26.51

EXAMPLE 9

Treatment of Viral Infection in Cell Culture in Vitro

Assays were performed in cell culture systems to determine the concentrations of compounds that are effective in preventing several kinds of viral infections. The assays are described below, and the results are presented in Table 1.

Abbreviations:

HSV-1 (herpes simplex virus type 1, strain Schooler), HSV-2 (herpes simplex virus type 2, strain 186), VZV (varicella zoster virus, strain ELLEN), HCMV (human cytomegalovirus, strain AD 169), MuLV (murine leukemia virus, strain CAS), HIV (human immunodeficiency virus, strain HTLV-IIIB).

Cell Culture Assays:

HSV-1, HSV-2, HCMV, and VZV antiviral assays: Virus was adsorbed to WI-38 cell culture monolayers in 6 well culture plates (Costar, Cambridge, MA) for 1 hour prior to addition of maintenance medium containing duplicate dilutions of the test compound. Inhibition of plaque development was evaluated on fixed and stained monolayers after 4 days incubation at 37° C. for HSV-1 and HSV-2 and after 6-7 days incubation at 37° C. for HCMV and VZV. $ID_{50}$ values were determined from the drug concentration which conferred at least a 50% plaque reduction compared to virus controls.

MuLV antiviral assay: Antiviral assays using MuLV were performed with some modification, as described by Rowe et al. and Shannon et al.. SC-1 cells were planted at approximately $2 \times 10^5$ cell per well in 6 well plates. After overnight incubation at 37° C., the cell cultures were sensitized with DEAE-Dextran for one hour at 37° C., rinsed and inoculated with MuLV. Cultures were re-fed with growth medium containing different concentrations of the test compound. After three more days at 37° C., cultures were re-fed with fresh medium plus test compounds and incubated at 37° C. for an additional 3 days. Cultures were then washed to remove medium, ultraviolet light irradiated, and planted with approximately $5 \times 10^5$ XC cells per well in cell growth medium containing the appropriate concentration of the test compound. The cultures were then incubated for an additional 4 days, with a re-feed using growth medium containing test compound at the second day following XC cell overlay. Finally the cultures were rinsed, stained and syncytial plaques were counted.

References:

Rowe, W.P., Pugh, W.E., and Hartley, J.W., (1970), Plaque Assay Techniques for Murine Leukemia Viruses, *Virology*, 42: 1136–1139.

Shannon, W.M, Brockman, R.W., Westbrook L., Shaddix, S., and Shabel, F.M., (1974) Inhibition of Gross Leukemia Virus-Induced Plaque Formation in XC Cells by 3-Deazauridine, *J. Natl., Cancer Inst.*, 2:199–205.

HIV antiviral assay: Suspensions of CEM(Nara and Fischinger, Nature, 332:469, 1988) cells were infected at a multiplicity of infection (e.g. virus/cell) of 0.12 with HIV (strain HTLV-III B). After adsorption for 1-2 hours at 37° C., infected cells were diluted in growth medium (RPMI 1640 containing the antibiotics penicillin plus streptomycin and 10% fetal calf serum) to a final cell concentration of $1 \times 10^4$ viable cells/ culture well in the presence of serial dilutions of the test compound, starting at 100µg/ml. Triplicate samples at each drug concentration were used. Cultures of uninfected CEM cells were similarly prepared and incubated with serial dilutions of test compound in duplicate. All assays were performed in 96 well disposable cell culture plates. Untreated (infected and uninfected) cells were included as controls. All cultures were incubated for 7 days at 37° C. in a humidified atmosphere containing 5% $CO_2$. Following incubation, viable cell numbers were counted in each well using a colorimetric assay following incubation of cells with XTT-PMS solution (XTT tetrazolium reagent plus phenazine methosulfate PMS).

Percent reduction of viral cytopathic effect (CPE) in drug treated compared to untreated virus infected cells, and percent reduction of cell viability in drug treated uninfected cells compared to untreated controls were calculated and plotted versus the drug concentrations tested. From these plots, the $ID_{50}$ (the minimum drug concentration that inhibits CPE by 50%) for each drug was calculated.

TABLE 1

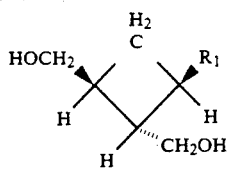

| R₁ | HSV-1 | HSV-2 | VZV | HCMV | MuLV | HIV |
|---|---|---|---|---|---|---|
| (imidazole-carboxamidine structure) | 0.08–0.2 | 0.04–0.08 | 0.2 | 3.8 | 3.8 | 30 |
| (adenine structure) | 8.0 | 4.0–8.0 | 0.8–2.0 | 0.8 | ND* | 6.8 |
| (5-iodouracil structure) | 6–14 | >284 | 14–28 | >284 | ND | ND |
| (cytosine structure) | 444 | 444 | 22 | 22–44 | ND | ND |
| (triazole-carboxamidine structure) | 7.5 | 7.5 | 3.8–38 | 376 | ND | ND |

TABLE 1-continued
[Structure diagram with HOCH₂, CH₂OH, R₁ substituents on cyclobutane]
| R₁ | ID₅₀ (μM) for the following viruses | | | | | |
|---|---|---|---|---|---|---|
| | HSV-1 | HSV-2 | VZV | HCMV | MuLV | HIV |
| [structure with HN, O, N, Br vinyl substituent] | 10–30 | >302 | 0.03–0.06 | >302 | ND | ND |
*ND = not determined
What we claim is:
1. A compound of the formula
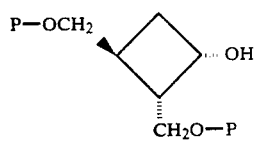
wherein P is a hydroxy protecting group.
2. A compound of the formula
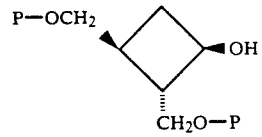
wherein P is a hydroxy protecting group.
* * * * *